(12) United States Patent
Biasella et al.

(10) Patent No.: US 12,740,821 B2
(45) Date of Patent: Sep. 22, 2026

(54) TISSUE TREATMENT DEVICES, SYSTEMS, AND METHODS

(71) Applicant: Fractyl Health, Inc., Lexington, MA (US)

(72) Inventors: Michael Biasella, Medford, MA (US); Sara Morneau, Lincoln, MA (US); Jay Caplan, Boston, MA (US); Michelle Riches, Leominster, MA (US); Philip Levin, Storrs, CT (US); Ryan Cahill, Scituate, MA (US); Keith Boudreau, North Andover, MA (US); Harith Rajagopalan, Wellesley Hills, MA (US); Brendan Zarechian, Reading, MA (US); Jeffrey Lesica, Holliston, MA (US); R. Maxwell Flaherty, Topsfield, MA (US); J. Christopher Flaherty, Nottingham, NH (US)

(73) Assignee: Fractyl Health, Inc., Burlington, MA (US)

( * ) Notice: Subject to any disclaimer, the term of this patent is extended or adjusted under 35 U.S.C. 154(b) by 685 days.

(21) Appl. No.: 17/859,137

(22) Filed: Jul. 7, 2022

(65) Prior Publication Data

US 2023/0165621 A1 Jun. 1, 2023

Related U.S. Application Data

(63) Continuation of application No. PCT/US2021/013072, filed on Jan. 12, 2021.

(Continued)

(51) Int. Cl.

*A61B 18/04* (2006.01)
*A61B 18/00* (2006.01)

(52) U.S. Cl.

CPC ...... *A61B 18/04* (2013.01); *A61B 2018/0022* (2013.01); *A61B 2018/00494* (2013.01);

(Continued)

(58) Field of Classification Search

CPC ................ A61B 18/04; A61B 18/1492; A61B 2018/0022; A61B 2018/00494;

(Continued)

(56) References Cited

U.S. PATENT DOCUMENTS 5,084,044 A 1/1992 Quint
5,190,540 A 3/1993 Lee (Continued)

FOREIGN PATENT DOCUMENTS

CA 2666661 C 1/2015
CN 1771888 A 5/2006

(Continued)

OTHER PUBLICATIONS

EP21741538.9 Extended European Search Report dated Dec. 18, 2023.

(Continued)

*Primary Examiner* — Daniel W Fowler
(74) *Attorney, Agent, or Firm* — Wolf, Greenfield & Sacks, P.C.

(57) ABSTRACT

Systems, devices and methods for performing medical procedures in the intestine of a patient are provided. A medical device for performing a treatment and/or a diagnostic procedure can include an elongate shaft assembly comprising at least a shaft assembly first section comprising a distal section of the shaft assembly, and a shaft assembly second section proximal to the first section, and a functional assembly positioned on the shaft assembly first section. Additional sections of the shaft assembly can be included, and each section can comprise a different construction, such as to (Continued)

achieve a different stiffness as described herein. Variable stiffness along the length of the shaft assembly can be provided to aid in translation of the device through the patient's GI tract (e.g. through the stomach and into the small intestine), as described herein.

17 Claims, 8 Drawing Sheets

Related U.S. Application Data

(60) Provisional application No. 62/960,340, filed on Jan. 13, 2020.

(52) U.S. Cl.
CPC ............... *A61B 2018/00577* (2013.01); *A61B 2018/046* (2013.01)

(58) Field of Classification Search
CPC .. A61B 2018/00577; A61B 2018/0212; A61B 2018/044
See application file for complete search history.

(56) References Cited

U.S. PATENT DOCUMENTS 5,423,754 A 6/1995 Cornelius et al.
5,471,982 A 12/1995 Edwards et al.
5,496,311 A 3/1996 Abele et al.
5,515,100 A 5/1996 Nogo
5,542,928 A 8/1996 Evans et al.
5,549,559 A 8/1996 Eshel
5,575,772 A 11/1996 Lennox
5,596,996 A * 1/1997 Johanson ............. A61M 25/09 600/585
5,704,934 A 1/1998 Neuwirth et al.
5,730,719 A 3/1998 Edwards
5,800,484 A 9/1998 Gough et al.
5,827,269 A 10/1998 Saadat
5,859,037 A 1/1999 Whitcomb et al.
5,869,037 A 2/1999 Crystal et al.
5,871,525 A 2/1999 Edwards et al.
5,879,347 A 3/1999 Saadat et al.
5,957,962 A 9/1999 Wallsten et al.
5,964,753 A 10/1999 Edwards
6,009,877 A 1/2000 Edwards
6,036,677 A * 3/2000 Javier, Jr. .......... A61M 25/0662 604/525
6,053,937 A 4/2000 Edwards et al.
6,056,744 A 5/2000 Edwards et al.
6,066,132 A 5/2000 Chen et al.
6,077,257 A 6/2000 Edwards et al.
6,112,123 A 8/2000 Kelleher et al.
6,293,909 B1 9/2001 Chu et al.
6,325,777 B1 12/2001 Zadno-Azizi et al.
6,325,798 B1 12/2001 Edwards et al.
6,338,726 B1 1/2002 Edwards et al.
6,358,245 B1 3/2002 Edwards et al.
6,402,744 B2 6/2002 Edwards et al.
6,405,732 B1 6/2002 Edwards et al.
6,409,723 B1 6/2002 Edwards
6,425,877 B1 * 7/2002 Edwards ............ A61B 18/1477 606/41
6,425,887 B1 7/2002 McGuckin et al.
6,443,947 B1 9/2002 Marko et al.
6,544,226 B1 4/2003 Gaiser et al.
6,547,787 B1 * 4/2003 Altman ................ A61N 1/0575 606/41
6,562,021 B1 * 5/2003 Derbin ............. A61M 25/0045 606/7
6,673,070 B2 1/2004 Edwards et al.
6,712,814 B2 3/2004 Edwards et al.
6,802,841 B2 10/2004 Utley et al.
6,905,496 B1 6/2005 Ellman et al.
6,962,587 B2 11/2005 Johnson et al.
6,974,456 B2 12/2005 Edwards et al.
7,077,841 B2 7/2006 Gaiser et al.
7,111,627 B2 9/2006 Stack et al.
7,122,031 B2 10/2006 Edwards et al.
7,125,407 B2 10/2006 Edwards et al.
7,156,860 B2 1/2007 Wallsten
7,165,551 B2 1/2007 Edwards et al.
7,241,295 B2 7/2007 Maguire
7,326,207 B2 2/2008 Edwards
7,371,215 B2 5/2008 Colliou et al.
7,387,626 B2 6/2008 Edwards et al.
7,422,587 B2 9/2008 Bek et al.
7,507,234 B2 3/2009 Utley et al.
7,507,238 B2 3/2009 Edwards et al.
7,530,979 B2 5/2009 Ganz et al.
7,556,628 B2 7/2009 Utley et al.
7,585,296 B2 9/2009 Edward et al.
7,632,268 B2 12/2009 Utley et al.
7,632,291 B2 12/2009 Stephens et al.
7,648,500 B2 1/2010 Edwards et al.
7,758,623 B2 7/2010 Dzeng et al.
7,762,977 B2 7/2010 Porter et al.
7,947,038 B2 5/2011 Edwards
7,959,627 B2 6/2011 Utley et al.
7,993,336 B2 8/2011 Jackson et al.
7,997,278 B2 8/2011 Utley et al.
8,012,149 B2 9/2011 Jackson et al.
8,066,689 B2 11/2011 Mitelberg et al.
8,152,803 B2 4/2012 Edwards et al.
8,177,853 B2 5/2012 Stack et al.
8,192,426 B2 6/2012 Stern et al.
8,251,992 B2 8/2012 Utley et al.
8,273,012 B2 9/2012 Wallace et al.
8,323,229 B2 12/2012 Shin et al.
8,364,237 B2 1/2013 Stone et al.
8,377,055 B2 2/2013 Jackson et al.
8,486,005 B2 7/2013 Yodfat et al.
8,641,711 B2 2/2014 Kelly et al.
8,740,894 B2 6/2014 Edwards
8,790,705 B2 7/2014 Geigle et al.
9,364,283 B2 6/2016 Utley et al.
9,555,020 B2 1/2017 Pasricha et al.
9,615,880 B2 4/2017 Gittard et al.
9,757,535 B2 9/2017 Rajagopalan et al.
9,844,641 B2 12/2017 Rajagopalan et al.
10,232,143 B2 3/2019 Rajagopalan et al.
10,299,857 B2 5/2019 Rajagopalan et al.
10,349,998 B2 7/2019 Levin et al.
10,610,663 B2 4/2020 Rajagopalan et al.
10,765,474 B2 9/2020 Kadamus et al.
10,864,352 B2 12/2020 Rajagopalan et al.
10,869,718 B2 12/2020 Rajagopalan et al.
10,980,590 B2 4/2021 Rajagopalan et al.
10,987,149 B2 4/2021 Rajagopalan et al.
2002/0077594 A1 6/2002 Chien et al.
2002/0192162 A1 12/2002 Green
2003/0040804 A1 2/2003 Stack et al.
2003/0093072 A1 5/2003 Friedman
2003/0153905 A1 8/2003 Edwards et al.
2003/0233065 A1 12/2003 Steward et al.
2004/0082859 A1 4/2004 Schaer
2004/0087936 A1 5/2004 Stern et al.
2004/0133256 A1 7/2004 Callister
2004/0148034 A1 7/2004 Kagan et al.
2004/0204768 A1 10/2004 Geitz
2004/0215180 A1 10/2004 Starkebaum et al.
2004/0215296 A1 10/2004 Ganz et al.
2004/0220559 A1 11/2004 Kramer et al.
2005/0096638 A1 5/2005 Starkebaum et al.
2005/0148997 A1 7/2005 Valley et al.
2005/0154386 A1 7/2005 West et al.
2005/0165437 A1 7/2005 Takimoto
2005/0171524 A1 8/2005 Stern et al.
2005/0192652 A1 9/2005 Cioanta et al.
2005/0203489 A1 9/2005 Saadat et al.
2005/0222558 A1 10/2005 Baxter et al.
2005/0245943 A1 11/2005 Zvuloni et al.

(56) References Cited

U.S. PATENT DOCUMENTS

2005/0251116 A1 11/2005 Steinke et al.
2005/0273090 A1 12/2005 Nieman et al.
2006/0070631 A1 4/2006 Scopton et al.
2006/0118127 A1 6/2006 Chinn
2006/0135963 A1 6/2006 Kick et al.
2006/0155261 A1 7/2006 Bek et al.
2006/0205992 A1 9/2006 Lubock et al.
2006/0247683 A1 11/2006 Danek et al.
2006/0293742 A1 12/2006 Dann et al.
2007/0016262 A1 1/2007 Gross et al.
2007/0032788 A1 2/2007 Edwards et al.
2007/0100355 A1 5/2007 Bonde et al.
2008/0045785 A1 2/2008 Oyatsu
2008/0107744 A1 5/2008 Chu
2008/0119788 A1 5/2008 Winter
2008/0125760 A1 5/2008 Gilboa
2008/0125803 A1 5/2008 Sadamasa et al.
2008/0147056 A1 6/2008 van der Weide et al.
2008/0161774 A1* 7/2008 Hastings ............. A61M 25/005 604/524
2008/0207994 A1 8/2008 Gonon
2008/0243112 A1 10/2008 De Neve
2008/0319504 A1 12/2008 Loushin et al.
2009/0012469 A1 1/2009 Nita
2009/0012518 A1 1/2009 Utley et al.
2009/0018533 A1 1/2009 Perkins et al.
2009/0048593 A1 2/2009 Ganz et al.
2009/0069805 A1 3/2009 Fischer et al.
2009/0270851 A1 10/2009 Babkin et al.
2010/0022891 A1 1/2010 Zuluaga et al.
2010/0030190 A1 2/2010 Singh
2010/0049192 A1* 2/2010 Holtz ................. A61N 1/36071 606/41
2010/0114087 A1 5/2010 Edwards et al.
2010/0114325 A1 5/2010 Yang et al.
2010/0168561 A1 7/2010 Anderson
2010/0168624 A1 7/2010 Sliwa
2010/0204673 A1 8/2010 Miller
2010/0204688 A1 8/2010 Hoey et al.
2010/0217151 A1 8/2010 Gostout et al.
2010/0256775 A1 10/2010 Belhe et al.
2010/0260703 A1 10/2010 Yankelson et al.
2010/0324552 A1* 12/2010 Kauphusman ... A61B 17/12036 606/41
2011/0046537 A1 2/2011 Errico et al.
2011/0091564 A1 4/2011 Chu
2011/0106273 A1 5/2011 Belhe et al.
2011/0160648 A1 6/2011 Hoey
2011/0172659 A1 7/2011 Brannan
2011/0184401 A1 7/2011 Iwata et al.
2011/0245822 A1 10/2011 Baxter et al.
2011/0319809 A1 12/2011 Smith
2012/0059364 A1 3/2012 Baust et al.
2012/0197245 A1 8/2012 Burnett et al.
2012/0271277 A1 10/2012 Fischell et al.
2012/0271301 A1 10/2012 Fischell et al.
2013/0071466 A1 3/2013 Chancellor et al.
2013/0178910 A1 7/2013 Azamian et al.
2014/0005647 A1* 1/2014 Shuffler ............ A61M 25/0136 29/592.1
2014/0031773 A1 1/2014 Mikkaichi
2014/0074077 A1 3/2014 Lane
2014/0088529 A1 3/2014 Bengtson
2014/0121646 A1 5/2014 Lodin et al.
2014/0135661 A1 5/2014 Garrison et al.
2014/0163664 A1 6/2014 Goldsmith
2014/0236120 A1 8/2014 Tsai et al.
2014/0255458 A1 9/2014 Li et al.
2014/0324037 A1 10/2014 Hoey et al.
2014/0336572 A1* 11/2014 Heisel ............... A61M 25/0045 604/95.04
2015/0045825 A1 2/2015 Caplan et al.
2015/0141987 A1 5/2015 Caplan et al.
2015/0148738 A1 5/2015 Caplan et al.
2015/0216581 A1* 8/2015 Duong ................... A61B 18/02 606/21
2015/0359594 A1 12/2015 Ben-Oren et al.
2016/0008050 A1 1/2016 Rajagopalan et al.
2016/0136393 A1 5/2016 Tsai et al.
2016/0310200 A1 10/2016 Wang
2016/0354144 A1 12/2016 Caplan et al.
2017/0007310 A1* 1/2017 Rajagopalan ........ A61B 5/0084
2017/0191035 A1 7/2017 Sia et al.
2017/0296252 A1 10/2017 Clark et al.
2017/0325666 A1 11/2017 Jiang et al.
2017/0348049 A1 12/2017 Vrba et al.
2018/0221622 A1 8/2018 Rajagopalan et al.
2020/0060758 A1 2/2020 Rajagopalan et al.
2020/0060942 A1 2/2020 Rajagopalan et al.
2020/0138505 A1 5/2020 Levin et al.
2020/0155217 A1 5/2020 Morneau et al.
2020/0261144 A1 8/2020 Caplan et al.
2020/0305972 A1 10/2020 Kadamus et al.
2020/0405388 A1 12/2020 Rajagopalan et al.
2021/0008336 A1 1/2021 Rajagopalan et al.
2021/0085390 A1 3/2021 Kadamus et al.
2021/0137995 A1 5/2021 Rajagopalan et al.
2021/0299404 A1 9/2021 Rajagopalan et al.
2021/0307816 A1 10/2021 Rajagopalan et al.

FOREIGN PATENT DOCUMENTS

CN 101212932 A 7/2008
EP 1698296 A1 9/2006
EP 1886634 A1 2/2008
EP 3071286 A1 9/2016
JP 2002503512 A 2/2002
JP 2003520068 A 7/2003
JP 2004500184 A 1/2004
JP 2006509536 A 3/2006
JP 2006136726 A 6/2006
JP 2007502690 A 2/2007
JP 2008515464 A 5/2008
JP 2010142661 A 7/2010
JP 2010533036 A 10/2010
JP 2011517599 A 6/2011
JP 2013543423 A 12/2013
JP 2014503256 A 2/2014
KR 20080013945 A 2/2008
WO WO-9418896 A1 9/1994
WO WO-9912489 A2 3/1999
WO WO-0207628 A2 1/2002
WO WO-02058577 A1 8/2002
WO WO-02096327 A2 12/2002
WO WO-02102453 A2 12/2002
WO WO-03033045 A2 4/2003
WO WO-03092609 A2 11/2003
WO WO-2004064600 A2 8/2004
WO WO-2006020370 A2 2/2006
WO WO-2007044244 A2 4/2007
WO WO-2007067919 A2 6/2007
WO WO-2008002654 A2 1/2008
WO WO-2010042461 A1 4/2010
WO WO-2010125570 A1 11/2010
WO WO-2011060301 A1 5/2011
WO WO-2012009486 A2 1/2012
WO WO-2012099974 A2 7/2012
WO WO-2013130655 A1 9/2013
WO WO-2013134541 A2 9/2013
WO WO-2013159066 A1 10/2013
WO WO-2014022436 A1 2/2014
WO WO-2014026055 A1 2/2014
WO WO-2014055997 A1 4/2014
WO WO-2014070136 A1 5/2014
WO WO-2015038973 A1 3/2015
WO WO-2015077571 A1 5/2015
WO WO-2015148541 A1 10/2015
WO WO-2016011269 A1 1/2016
WO WO-2017004432 A1 1/2017
WO WO-2018022404 A1 2/2018
WO WO-2018089773 A1 5/2018
WO WO-2019018362 A1 1/2019
WO WO-2019136240 A1 7/2019

(56) References Cited

FOREIGN PATENT DOCUMENTS

WO WO-2020072506 A1 4/2020
WO WO-2020205844 A1 10/2020
WO WO-2021081072 A1 4/2021
WO WO-2021146190 A1 7/2021

OTHER PUBLICATIONS

Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.
Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.
Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.
EP12736438.8 The Extended European Search Report dated Nov. 22, 2016.
EP14844285.8 The Extended European Search Report dated Apr. 25, 2017.
EP20150391.9 The Extended European Search Report dated Aug. 20, 2020.
EP20159816.6 The Extended European Search Report dated Aug. 17, 2020.
European search report and search opinion dated Mar. 8, 2016 for EP Application No. 13825257.2.
European search report and search opinion dated Mar. 17, 2016 for EP Application No. 13827149.9.
European search report and search opinion dated Aug. 4, 2015 for EP Application No. 13755156.0.
European Search Report and Search Opinion dated Aug. 7, 2017 for European Patent Application No. EP14864511.2.
European Search Report and Search Opinion dated Aug. 7, 2017 for European Patent Application No. EP15768945.6.
European search report and search opinion dated Nov. 25, 2015 for EP Application No. 13777572.2.
European search report with written opinion dated Feb. 1, 2018 for EP Application No. 15822378.
European search report with written opinion dated Dec. 2, 2016 for EP Application No. 14807116.
Final Office action dated Mar. 22, 2019 for U.S. Appl. No. 14/917,243.
Final Office action dated Apr. 5, 2019 for U.S. Appl. No. 14/609,334.
Final Office action dated Jun. 17, 2019 for U.S. Appl. No. 14/609,332.
Final Office action dated Jul. 10, 2019 for U.S. Appl. No. 15/274,948.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.
Grikscheit, et al. Tissue-engineered small intestine improves recovery after massive small bowel resection. Ann Surg., 2004, 240:748-754.
International search report and written opinion dated Feb. 20, 2015 for PCT Application No. US2014/711601.
International search report and written opinion dated Jun. 21, 2013 for PCT Application No. US2013/028082.
International search report and written opinion dated Jun. 26, 2015 for PCT Application No. US2015/022293.
International search report and written opinion dated Jul. 13, 2012 for PCT Application No. US2012/021739.
International search report and written opinion dated Aug. 8, 2013 for PCT Application No. US2013/037485.
International Search Report and Written Opinion dated Sep. 22, 2016 for International PCT Patent Application No. PCT/US2016/040512.
International search report and written opinion dated Oct. 23, 2015 for PCT/US2015/040775.
International search report and written opinion dated Nov. 8, 2013 for PCT Application No. US2013/052786.
International search report and written opinion dated Nov. 11, 2013 for PCT Application No. US2013/054219.
International search report and written opinion dated Dec. 24, 2014 for PCT Application No. US2014/055514.
International search report and written opinion dated Dec. 30, 2013 for PCT Application No. US2013/063753.
International search report dated Dec. 3, 2014 for PCT Application No. US2014/040957.
International search report with written opinion dated Jan. 9, 2018 for PCT/US2017/061074.
Miyawaki, et al. Inhibition of gastric inhibitory polypeptide signaling prevents obesity. Nat Med. Jul. 2002;8(7):738-42. Epub Jun. 17, 2002.
Notice of Allowance dated Jul. 7, 2017 for U.S. Appl. No. 15/274,764.
Notice of Allowance dated Sep. 14, 2017 for U.S. Appl. No. 15/274,809.
Office Action date Jul. 11, 2018 for U.S. Appl. No. 14/917,243.
Office Action date Aug. 9, 2018 for U.S. Appl. No. 14/673,565.
Office action dated Jan. 8, 2018 for U.S. Appl. No. 14/609,334.
Office Action dated Jan. 13, 2017 for U.S. Appl. No. 14/609,332.
Office action dated Feb. 29, 2016 for U.S. Appl. No. 14/609,334.
Office action dated Mar. 7, 2019 for U.S. Appl. No. 13/945,138.
Office Action dated Mar. 7, 2017 for U.S. Appl. No. 15/274,764.
Office Action dated Mar. 7, 2017 for U.S. Appl. No. 15/274,809.
Office action dated Mar. 7, 2019 for U.S. Appl. No. 14/673,565.
Office action dated Mar. 12, 2015 for U.S. Appl. No. 13/945,138.
Office action dated Mar. 19, 2018 for U.S. Appl. No. 14/470,503.
Office Action dated Mar. 23, 2017 for U.S. Appl. No. 13/945,138.
Office action dated Mar. 28, 2016 for U.S. Appl. No. 14/673,565.
Office action dated Apr. 4, 2018 for U.S. Appl. No. 15/156,585.
Office action dated May 16, 2019 for U.S. Appl. No. 14/515,324.
Office action dated May 18, 2018 for U.S. Appl. No. 14/956,710.
Office Action dated May 31, 2017 for U.S. Appl. No. 15/274,764.
Office action dated Jun. 6, 2019 for U.S. Appl. No. 15/683,713.
Office Action dated Jun. 21, 2017 for U.S. Appl. No. 14/515,324.
Office Action dated Jun. 21, 2017 for U.S. Appl. No. 14/609,334.
Office Action dated Jun. 30, 2017 for U.S. Appl. No. 14/470,503.
Office action dated Aug. 5, 2015 for U.S. Appl. No. 13/945,138.
Office action dated Sep. 7, 2018 for U.S. Appl. No. 14/609,332.
Office Action dated Sep. 23, 2016 for U.S. Appl. No. 14/515,324.
Office action dated Oct. 4, 2018 for U.S. Appl. No. 14/515,324.
Office Action dated Oct. 7, 2016 for U.S. Appl. No. 13/945,138.
Office Action dated Nov. 2, 2017 for U.S. Appl. No. 15/156,585.
Office action dated Nov. 2, 2018 for U.S. Appl. No. 14/609,334.
Office Action dated Nov. 15, 2016 for U.S. Appl. No. 14/609,334.
Office action dated Nov. 16, 2017 for U.S. Appl. No. 14/609,332.
Office action dated Nov. 30, 2015 for U.S. Appl. No. 13/945,138.
Office action dated Nov. 30, 2017 for U.S. Appl. No. 14/673,565.
Office action dated Dec. 17, 2015 for U.S. Appl. No. 14/515,324.
Office action dated Dec. 18, 2017 for U.S. Appl. No. 14/515,324.
Office action dated Dec. 18, 2018 for U.S. Appl. No. 14/470,503.
Office action dated Dec. 19, 2017 for U.S. Appl. No. 13/945,138.
PCT/US14/66829 International Search Report dated Feb. 20, 2015.
PCT/US2019/012338 International Search Report dated Apr. 15, 2019.
PCT/US2021/013072 International Search Report and Written Opinion dated Apr. 1, 2021.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Rubino, et al. Potential of surgery for curing type 2 diabetes mellitus. Ann Surg. Nov. 2002;236(5):554-9.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Semkova, et al. Autologous transplantation of genetically modified iris pigment epithelial cells: A promising concept for the treatment

(56) References Cited

OTHER PUBLICATIONS of age-related macular degeneration and other disorders of the eye. Proc Natl Acad Sci U S A. Oct. 1, 2002; 99(20): 13090-13095.
Sen, et al. Autologous transplantation of endothelial progenitor cells genetically modified by adeno-associated viral vector delivering insulin-like growth factor-1 gene after myocardial infarction. Hum Gene Ther. Oct. 2010;21(10):1327-34.
Tolman, et al. Spectrum of liver disease in type 2 diabetes and management of patients with diabetes and liver disease. Diabetes care 30.3 (2007): 734-743.
Tomizawa, et al. Clinical Outcome of Endoscopic Mucosal Resection (EMR) of Sporadic, Non-Ampullary Duodenal Adenoma (SNADA): Predictor Analysis of Safety and Efficacy From a High Volume U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
U.S. Appl. No. 14/917,243 Office Action dated Jun. 5, 2020.
U.S. Appl. No. 13/945,138 Notice of Allowance dated Dec. 22, 2020.
U.S. Appl. No. 14/515,324 Office Action dated Dec. 4, 2020.
U.S. Appl. No. 14/609,334 Notice of Allowance dated Dec. 10, 2020.
U.S. Appl. No. 14/609,334 Office Action dated Oct. 29, 2020.
U.S. Appl. No. 14/673,565 Office Action dated Dec. 24, 2020.
U.S. Appl. No. 14/673,565 Office Action dated Jun. 12, 2020.
U.S. Appl. No. 15/274,948 Notice of Allowance dated May 14, 2020.
U.S. Appl. No. 15/274,948 Office Action dated Nov. 20, 2018.
U.S. Appl. No. 15/406,572 Notice of Allowance dated Oct. 28, 2020.
U.S. Appl. No. 15/406,572 Office Action dated Apr. 14, 2020.
U.S. Appl. No. 15/406,572 Office Action dated Feb. 7, 2019.
U.S. Appl. No. 15/406,572 Office Action dated Nov. 15, 2019.
U.S. Appl. No. 15/917,480 Notice of Allowance dated Dec. 17, 2020.
U.S. Appl. No. 15/917,480 Office Action dated Nov. 20, 2020.
U.S. Appl. No. 16/267,771 Notice of Allowance dated Aug. 10, 2020.
U.S. Appl. No. 16/711,236 Office Action dated Dec. 10, 2020.
U.S. Appl. No. 16/900,563 Notice of Allowance dated Dec. 17, 2020.
U.S. Appl. No. 16/900,563 Office Action dated Nov. 9, 2020.
U.S. Appl. No. 13/945,138 Office Action dated Dec. 10, 2019.
U.S. Appl. No. 14/515,324 Office Action dated Mar. 31, 2020.
U.S. Appl. No. 14/609,334 Office Action dated Jan. 8, 2020.
U.S. Appl. No. 15/683,713 Notice of Allowance dated Mar. 10, 2020.
U.S. Appl. No. 15/683,713 Notice of Allowance dated Nov. 27, 2019.
U.S. Appl. No. 15/683,713 Office Action dated Oct. 10, 2019.
U.S. Appl. No. 15/917,480 Office Action dated Jan. 10, 2020.
U.S. Appl. No. 16/267,771 Office Action dated Feb. 6, 2020.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017vol. 152, Issue 5, Supplement 1, p. S825. DOI: http://dx.doi.org/10.1016/S0016-5085(17)32851-2.

* cited by examiner

10
VACUUM SUPPLY 110
INJECTATE SUPPLY 120
INFLATION FLUID SUPPLY 130
ABLATIVE FLUID SUPPLY 140
NEUTRALIZING FLUID SUPPLY 150
FLUID REMOVAL PUMP 160
INSUFFLATION SUPPLY 170
FUNCTIONAL FLUID SUPPLY 180
ENDOSCOPE 50
GUIDEWIRE 60
IMAGING DEVICE 70
AGENT 80
MARKER 90
195/ 700a
100
200
300
400
500
600

MUSCULARIS LAYER
2nd SUBMUCOSAL EXPANDED TISSUE VOLUME
1st SUBMUCOSAL EXPANDED TISSUE VOLUME
SUBMUCOSAL LAYER
MUCOSAL LAYER
500
LENGTH OF ABLATION PERIPHERY
LENGTH OF EXPANDED TISSUE PERIPHERY
200

TISSUE TREATMENT DEVICES, SYSTEMS, AND METHODS

CROSS-REFERENCE TO RELATED APPLICATIONS

This application is a continuation of PCT Application No. PCT/US2021/13072, filed Jan. 12, 2021, which claims the benefit of U.S. Application No. 62/960,340, filed Jan. 13, 2020, the content of which is incorporated herein by reference in its entirety.

This application is related to: U.S. patent application Ser. No. 13/945,138, entitled "Devices and Methods for the Treatment of Tissue", filed Jul. 18, 2013; U.S. patent application Ser. No. 15/917,480, entitled "Devices and Methods for the Treatment of Tissue", filed Mar. 9, 2018; U.S. patent application Ser. No. 16/438,362, entitled "Heat Ablation Systems, Devices and Methods for the Treatment of Tissue", filed Jun. 11, 2019; U.S. patent application Ser. No. 14/515,324, entitled "Tissue Expansion Devices, Systems and Methods", filed Oct. 15, 2014; U.S. patent application Ser. No. 16/711,236, entitled "Electrical Energy Ablation Systems, Devices and Methods for the Treatment of Tissue", filed Dec. 11, 2019; U.S. patent application Ser. No. 14/609,334, entitled "Ablation Systems, Devices, and Methods for the Treatment of Tissue", filed Jan. 29, 2015; U.S. patent application Ser. No. 14/673,565, entitled "Methods, Systems and Devices for Performing Multiple Treatments on a Patient", filed Mar. 30, 2015; U.S. patent application Ser. No. 16/379,554, entitled "Methods, Systems and Devices for Reducing the Luminal Surface Area of the Gastrointestinal Tract", filed Apr. 9, 2019; U.S. patent application Ser. No. 14/917,243, entitled "Systems, Methods and Devices for Treatment of Target Tissue", filed Mar. 7, 2016; U.S. patent application Ser. No. 16/742,645, entitled "Intestinal Catheter Device and System", filed Jan. 14, 2020; United States Provisional Patent Application Ser. No. 62/961,340, entitled "Automated Tissue Treatment Devices, Systems, and Methods", filed Jan. 15, 2020; U.S. patent application Ser. No. 16/900,563, entitled "Injectate Delivery Devices, Systems and Methods", filed Jun. 12, 2020; U.S. patent application Ser. No. 16/798,117, entitled "Systems, Devices and Methods for Performing Medical Procedures in the Intestine", filed Feb. 21, 2020; U.S. patent application Ser. No. 15/812,969, entitled "Systems, Devices and Methods for Performing Medical Procedures in the Intestine", filed Nov. 14, 2017; U.S. patent application Ser. No. 16/400,491, entitled "Systems, Devices and Methods for Performing Medical Procedures in the Intestine", filed May 1, 2019; U.S. patent application Ser. No. 16/905,274, entitled "Material Depositing System for Treating a Patient", filed Jun. 18, 2020; International PCT Patent Application Serial Number PCT/US2019/54088, entitled "Systems and Methods for Deposition Material in a Patient", filed Oct. 1, 2019; International PCT Patent Application Serial Number PCT/US2020/025925, entitled "Systems, Devices and Methods for Treating Metabolic Medical Conditions", filed Mar. 31, 2020; U.S. Provisional Patent Application Ser. No. 62/991,219, entitled "Systems, Devices and Methods for Treating Diabetes", filed Mar. 18, 2020; U.S. Provisional Patent Application Ser. No. 63/042,356, entitled "Tissue Treatment System with Fluid Delivery Console", filed Jun. 22, 2020; U.S. Provisional Patent Application Ser. No. 63/076,737, entitled "Systems, Devices and Methods for Treating Diabetes", filed Sep. 10, 2020; U.S. Provisional Patent Application Ser. No. 63/085,375, entitled "Systems, Devices and Methods for Treating Diabetes", filed Sep. 30, 2020; International PCT Patent Application Serial Number PCT/US2020/056627, entitled "Systems, Devices, and Methods for Performing Medical Procedures in the Intestine", filed Oct. 21, 2020; U.S. patent application Ser. No. 17/095,108, entitled "Systems, Devices and Methods for the Creation of a Therapeutic Restriction in the Gastrointestinal Tract", filed Nov. 11, 2020; U.S. patent application Ser. No. 17/096,855, entitled "Methods and Systems for Treating Diabetes and Related Diseases and Disorders", filed Nov. 12, 2020; and U.S. patent application Ser. No. 17/110,720, entitled "Injectate Delivery Devices, Systems and Methods", filed Dec. 3, 2020; the contents of each of which is incorporated herein by reference in its entirety for all purposes.

BACKGROUND OF THE INVENTION

Field of the Invention

The present invention relates generally to devices, systems, and method for treating tissue, and in particular, catheter devices for treating tissue of the gastrointestinal tract of a patient.

Various medical devices are inserted through the patient's mouth and advanced into the stomach and more distal locations to perform a medical procedure, such as a diagnostic and/or therapeutic procedure. These devices are often difficult to advance, retract, rotate, and/or otherwise manipulate, often due to the tortuosity of the pathway into which they are placed. There is a need for medical devices that have enhanced performance under these challenging conditions.

BRIEF SUMMARY OF THE INVENTION

According to an aspect of the present inventive concepts, a device for performing a medical procedure in the intestine of a patient comprises: an elongate shaft assembly comprising at least a shaft assembly first section comprising a distal section of the shaft assembly, and a shaft assembly second section proximal to the first section, and a functional assembly positioned on the shaft assembly first section; wherein the shaft assembly first section comprises a first stiffness. The shaft assembly second section comprises a second stiffness, and the first stiffness is less stiff than the second stiffness.

In some embodiments, the intestine comprises at least a portion of the small intestine. The intestine can comprise at least a portion of the duodenum.

In some embodiments, the shaft assembly comprises a multi lumen shaft. The elongate shaft assembly can further comprise at least one conduit positioned within a lumen of the multi lumen shaft.

In some embodiments, the shaft assembly first section comprises a length of at least 2 inches.

In some embodiments, the shaft assembly second section comprises a length of at least 10 inches.

In some embodiments, the shaft assembly further comprises a shaft assembly third section proximal to the shaft assembly second section. The shaft assembly third section can comprise a length of at least 32 inches. The shaft assembly third section can be longer than the shaft assembly second section and the shaft assembly second section can be longer than the shaft assembly first section. The shaft assembly first section can comprise a material with a durometer of approximately 40 D, the shaft assembly second section can comprise a material with a durometer of approximately 55 D, and the shaft assembly third section can comprise a material with a durometer of approximately 63 D. The shaft assembly third section can comprise a length of approximately 57 inches, the shaft assembly second section can comprise a length of approximately 10 inches, and the shaft assembly first section can comprise a length of approximately 5 inches. The shaft assembly first section can comprise a material with a durometer of approximately 40 D, the shaft assembly second section can comprise a material with a durometer of approximately 55 D, and the shaft assembly third section can comprise a material with a durometer of approximately 63 D. The shaft assembly can be constructed and arranged to bend as follows: a midpoint of a 2 inch span of a section deflects a distance of approximately 0.125 inches when the following force is applied: at least 10 lbf, at least 13 lbf, or at least 16 lbf applied to the shaft assembly third section; at least 8 lbf, at least 10 lbf, or at least 11 lbf applied to the shaft assembly second section; and/or at most 14 lbf, at most 11 lbf, or at most 8 lbf applied to the shaft assembly first section. The shaft assembly can be constructed and arranged to bend as follows: a midpoint of a 2 inch span of the first section deflects a distance of approximately 0.125 inches when a first force is applied; and a midpoint of a 2 inch span of the second section deflects a distance of approximately 0.125 inches when a second force is applied; and the second force can be at least 3 lbf more than the first force. The shaft assembly can be constructed and arranged to bend as follows: a midpoint of a 2 inch span of the second section deflects a distance of approximately 0.125 inches when a second force is applied; and a midpoint of a 2 inch span of the third section deflects a distance of approximately 0.125 inches when a third force is applied; and the third force can be at least 4 lbf more than the second force. The shaft assembly can be constructed and arranged to bend as follows: a midpoint of a 2 inch span of the first section deflects a distance of approximately 0.125 inches when a first force is applied; and a midpoint of a 2 inch span of the third section deflects a distance of approximately 0.125 inches when a third force is applied; and the third force can be at least 7 lbf more than the first force.

In some embodiments, the shaft assembly further comprises a fourth section comprising a distal tip fixedly attached to a distal end of the shaft assembly first section, and the fourth section comprises a stiffness less than the stiffness of the shaft assembly first section. The distal tip can comprise a tapered distal tip.

In some embodiments, the functional assembly is configured to expand tissue within the intestine of the patient.

In some embodiments, the functional assembly is configured to ablate tissue within the intestine of the patient.

In some embodiments, the functional assembly is configured to remove tissue within the intestine of the patient.

In some embodiments, the functional assembly is configured to expand and ablate tissue within the intestine of the patient.

In some embodiments, the functional assembly comprises a balloon. The functional assembly can be configured to ablate tissue within the intestine of the patient with a hot fluid.

In some embodiments, the device further comprises an injection assembly including at least one needle, at least one port, and at least one fluid delivery tube.

According to another aspect of the present inventive concepts, a device for performing a medical procedure in the intestine of a patient comprises: an elongate shaft assembly comprising a proximal portion, a distal portion, and at least two lumens therethrough, a functional assembly positioned on the distal portion of the elongate shaft assembly, and an injection assembly comprising at least one port attached to the functional assembly and at least one conduit operably connecting one of the at least two lumens of the shaft assembly to the at least one port. The at least one conduit is rotated about the distal portion of the shaft assembly.

In some embodiments, the at least one port comprises at least two ports and the at least one conduit comprises at least two conduits.

In some embodiments, the at least one port comprises at least three ports and the at least one conduit comprises at least three conduits.

In some embodiments, the at least one conduit is rotated at least 25°, at least 50°, or at least 100° about the distal portion of the shaft assembly. The at least one conduit can be rotated approximately 180° about the distal portion of the shaft assembly.

In some embodiments, the at least one conduit comprises a biased shape. The biased shape can comprise an "S" shape.

In some embodiments, the at least one conduit comprises at least one lumen therethrough. The at least one lumen can comprise at least two lumens.

In some embodiments, the shaft assembly further comprises a manifold, and the manifold operably connects at least one of the at least two shaft lumens to the at least one conduit.

The technology described herein, along with the attributes and attendant advantages thereof, will best be appreciated and understood in view of the following detailed description taken in conjunction with the accompanying drawings in which representative embodiments are described by way of example.

INCORPORATION BY REFERENCE

All publications, patents, and patent applications mentioned in this specification are herein incorporated by reference to the same extent as if each individual publication, patent, or patent application was specifically and individually indicated to be incorporated by reference. The content of all publications, patents, and patent applications mentioned in this specification are herein incorporated by reference in their entirety for all purposes.

DETAILED DESCRIPTION OF THE DRAWINGS

Figure 1:
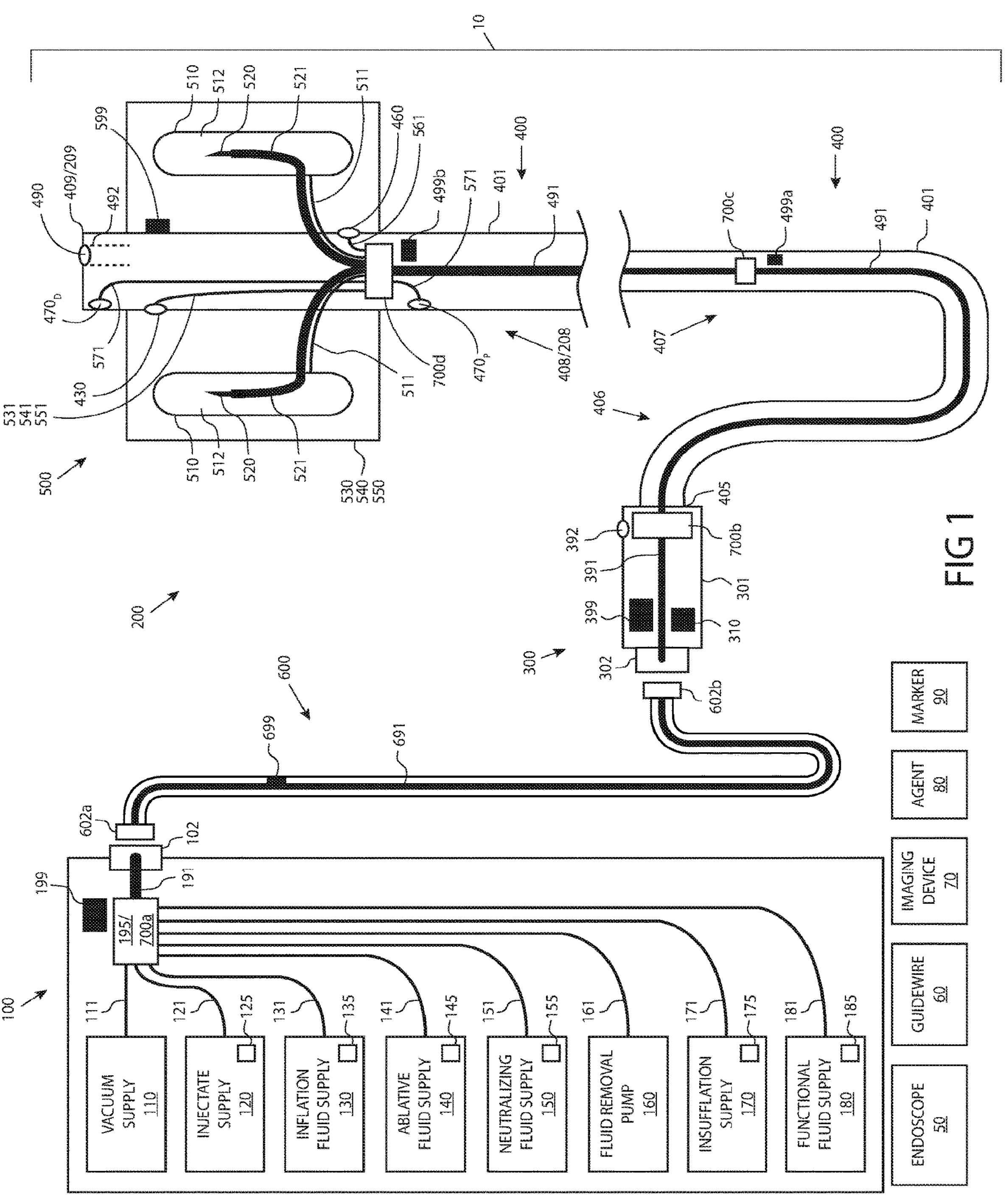
FIG. 1 illustrates a system for treating and/or diagnosing gastrointestinal tissue, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence. Correspondingly, the terms "prevent", "preventing", and "prevention" shall include the acts of "reduce", "reducing", and "reduction", respectively.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "one or more", where used herein can mean one, two, three, four, five, six, seven, eight, nine, ten, or more, up to any number.

The terms "and combinations thereof" and "and combinations of these" can each be used herein after a list of items that are to be included singly or collectively. For example, a component, process, and/or other item selected from the group consisting of: A; B; C; and combinations thereof, shall include a set of one or more components that comprise: one, two, three or more of item A; one, two, three or more of item B; and/or one, two, three, or more of item C.

In this specification, unless explicitly stated otherwise, "and" can mean "or", and "or" can mean "and". For example, if a feature is described as having A, B, or C, the feature can have A, B, and C, or any combination of A, B, and C. Similarly, if a feature is described as having A, B, and C, the feature can have only one or two of A, B, or C.

As used herein, when a quantifiable parameter is described as having a value "between" a first value X and a second value Y, it shall include the parameter having a value of: at least X, no more than Y, and/or at least X and no more than Y. For example, a length of between 1 and 10 shall include a length of at least 1 (including values greater than 10), a length of less than 10 (including values less than 1), and/or values greater than 1 and less than 10.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As used herein, the terms "about" or "approximately" shall refer to ±10%.

As used herein, the term "threshold" refers to a maximum level, a minimum level, and/or range of values correlating to a desired or undesired state. In some embodiments, a system parameter is maintained above a minimum threshold, below a maximum threshold, within a threshold range of values, and/or outside a threshold range of values, such as to cause a desired effect (e.g. efficacious therapy) and/or to prevent or otherwise reduce (hereinafter "prevent") an undesired event (e.g. a device and/or clinical adverse event). In some embodiments, a system parameter is maintained above a first threshold (e.g. above a first temperature threshold to cause a desired therapeutic effect to tissue) and below a second threshold (e.g. below a second temperature threshold to prevent undesired tissue damage). In some embodiments, a threshold value is determined to include a safety margin, such as to account for patient variability, system variability, tolerances, and the like. As used herein, "exceeding a threshold" relates to a parameter going above a maximum threshold, below a minimum threshold, within a range of threshold values and/or outside of a range of threshold values.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

As used herein, the term "functional element" is to be taken to include one or more elements constructed and arranged to perform a function. A functional element can comprise a sensor and/or a transducer. In some embodiments, a functional element is configured to deliver energy and/or otherwise treat tissue (e.g. a functional element configured as a treatment element). Alternatively or additionally, a functional element (e.g. a functional element comprising a sensor) can be configured to record one or more parameters, such as a patient physiologic parameter; a patient anatomical parameter (e.g. a tissue geometry parameter); a patient environment parameter; and/or a system parameter. In some embodiments, a sensor or other functional element is configured to perform a diagnostic function (e.g. to gather data used to perform a diagnosis). In some embodiments, a functional element is configured to perform a therapeutic function (e.g. to deliver therapeutic energy and/or a therapeutic agent). In some embodiments, a functional element comprises one or more elements constructed and arranged to perform a function selected from the group consisting of: deliver energy; extract energy (e.g. to cool a component); deliver a drug or other agent; manipulate a system component or patient tissue; record or otherwise sense a parameter such as a patient physiologic parameter or a system parameter; and combinations of one or more of these. A functional element can comprise a fluid and/or a fluid delivery system. A functional element can comprise a reservoir, such as an expandable balloon or other fluid-maintaining reservoir. A "functional assembly" can comprise an assembly constructed and arranged to perform a function, such as a diagnostic and/or therapeutic function. A functional assembly can comprise an expandable assembly. A functional assembly can comprise one or more functional elements.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as: light (e.g. a transducer comprising a light emitting diode or light bulb), sound (e.g. a transducer comprising a piezo crystal configured to deliver ultrasound energy); pressure (e.g. an applied pressure or force); heat energy; cryogenic energy; chemical energy; mechanical energy (e.g. a transducer comprising a motor or a solenoid); magnetic energy; and/or a different electrical signal (e.g. different than the input signal to the transducer). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

As used herein, the term "fluid" can refer to a liquid, gas, gel, or any flowable material, such as a material which can be propelled through a lumen, a needle, a nozzle, and/or an opening.

As used herein, the term "material" can refer to a single material, or a combination of two, three, four, or more materials.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Terms defined in the present disclosure are only used for describing specific embodiments of the present disclosure and are not intended to limit the scope of the present disclosure. Terms provided in singular forms are intended to include plural forms as well, unless the context clearly indicates otherwise. All of the terms used herein, including technical or scientific terms, have the same meanings as those generally understood by an ordinary person skilled in the related art, unless otherwise defined herein. Terms defined in a generally used dictionary should be interpreted as having meanings that are the same as or similar to the contextual meanings of the relevant technology and should not be interpreted as having ideal or exaggerated meanings, unless expressly so defined herein. In some cases, terms defined in the present disclosure should not be interpreted to exclude the embodiments of the present disclosure.

Provided herein are systems, devices and method for performing medical procedures in the intestine of a patient. A medical device for performing a treatment and/or a diagnostic procedure can include an elongate shaft assembly comprising at least a shaft assembly first section comprising a distal section of the shaft assembly, and a shaft assembly second section proximal to the first section, and a functional assembly positioned on the shaft assembly first section. Additional sections of the shaft assembly can be included, and each section can comprise a different construction, such as to achieve a different stiffness as described herein. Variable stiffness along the length of the shaft assembly can be provided to aid in translation of the device through the patient's GI tract (e.g. through the stomach and into the small intestine), as described herein. The medical device can include a shaft assembly comprising a proximal portion and a distal portion, with at least two lumens passing therethrough. A functional assembly for performing a treatment and/or a diagnosis can be positioned on the distal portion of the shaft assembly. An injection assembly can also be included, and the assembly can comprise at least one attached port and at least one conduit operably connecting one of the at least two lumens of the shaft assembly to the at least one port. The at least one conduit can be rotated about the distal portion of the shaft assembly.

Referring now to FIG. 1, a system for treating and/or diagnosing ("treating" herein) gastrointestinal tissue is illustrated, consistent with the present inventive concepts. System 10 includes console 100 that operably attaches to a catheter, catheter 200. System 10 and catheter 200 can be used by an operator (e.g. one or more clinicians) to perform a medical procedure, such as a therapeutic procedure and/or a diagnostic procedure. Catheter 200 can be constructed and arranged to treat and/or diagnose target tissue, such as tissue of the small intestine (e.g. mucosal tissue of the duodenum and/or jejunum) and/or other locations within the gastrointestinal (GI) tract. Catheter 200 can be constructed and arranged to ablate or remove tissue, such as by delivering energy and/or an agent (e.g. a necrotic agent) to tissue. Alternatively or additionally, catheter 200 can be constructed and arranged to expand one or more layers of tissue of the GI tract, such as when a submucosal tissue expansion procedure is performed in one segment of the GI tract after which an energy delivery to mucosal tissue is performed in that same segment. Catheter 200 can be constructed and arranged to treat multiple relatively contiguous segments ("contiguous segments" herein) or non-contiguous segments of the GI tract. In some embodiments, two or more axial segments of submucosal tissue of intestine are expanded, after which a single ablation procedure is performed (e.g. an ablation of a length of tissue of similar or lesser length as compared to the cumulative length of submucosal tissue expanded, such as when the length treated by a single ablation step is greater than the length expanded in a single tissue expansion step), such as is described herein in reference to FIGS. 1B and 1C. Alternatively or additionally, a single axial segment of submucosal tissue of the intestine is expanded, after which a single ablation procedure is performed (e.g. in the same axial location without movement of catheter 200). In some embodiments, a pre-treatment (e.g. pre-cooling) procedure is performed during the submucosal expansion, after which the tissue is treated (e.g. ablated via heat and/or other thermal ablation). Pre-treating of the target tissue and/or tissue proximate the target tissue is described herein. In some embodiments, an ablation procedure is performed in a segment of the intestine where a submucosal tissue expansion has not been performed.

In some embodiments, system 10 comprises one or more body access devices, such as endoscope 50 shown. Catheter 200 can be configured to be inserted through one or more working channels of endoscope 50 and/or alongside endoscope 50. In some embodiments, catheter 200 is inserted through a sheath attached to endoscope 50. Catheter 200 can comprise a length such that it can be inserted through the patient's mouth and into one or more locations within the stomach, the duodenum, the jejunum and/or the ileum.

In some embodiments, system 10 comprises one or more guidewires, such as guidewire 60 shown. In these embodiments, catheter 200 can be advanced over guidewire 60, such as by using standard over-the-wire techniques, through one or more lumens of catheter 200.

Console 100 can include one or more conduits, conduit 191 configured to transport fluid to and/or from console 100. Console 100 can include pump assembly 195 that includes one or more pumps or other fluid delivery mechanisms ('pump" herein) that deliver fluid (e.g. a liquid, a gas, and/or a gel) into one or more fluid pathways or other locations within catheter 200. Console 100 can include one or more reservoirs that store these fluids to be delivered. Alternatively or additionally, console 100 can be attachable to a fluid-storing reservoir separate from console 100 (or positioned in a second housing of console 100). Pump assembly 195 and/or another component of console 100 can include one or more pumps or other fluid removal mechanisms ("pump" herein) that extract fluid from one or more lumens or other locations within catheter 200. Console 100 can include one or more reservoirs that store these removed fluids, or they can be stored in a reservoir separate from console 100 (or positioned in a second housing of console 100). Pump assembly 195 and/or another component of console 100 can include one or more pumps or other vacuum generating mechanisms ("pump" herein) that generate a vacuum that can cause a negative pressure within one or more lumens or other locations within catheter 200.

Console 100 can comprise one or more discrete components, such as one or more components each with a discrete (i.e. separate) housing that surrounds one or more pumps and/or reservoirs.

In some embodiments, console 100 comprises vacuum supply 110. Vacuum supply 110 can comprise one or more pumps configured to generate a vacuum within catheter 200 and/or other component of system 10. In some embodiments, vacuum supply 110 includes one or more reservoirs configured to reduce variations in vacuum pressure. Vacuum supply 110 can provide a vacuum to one, two, three or more ports configured to engage tissue, such as tissue capture chambers 510 described herein. Vacuum supply 110 can be configured to provide a vacuum pressure of between −2 psi and −14.7 psi, such as between −4 psi and −14.7 psi. In some embodiments, system 10 can be configured to operate with vacuum supply 110 providing a vacuum pressure of between −6 psi and −12.5 psi. Additionally or alternatively, vacuum supply 110 and/or another component of console 100 can comprise at least one sensor, such as a sensor-based functional element 199, configured to monitor the pressure of vacuum supply 110, and provide an alert (e.g. an alert to the operator and/or enter a system wide alert mode) if the vacuum pressure is insufficient or otherwise undesired (e.g. if the vacuum pressure is above or below a desired level, an expected level, and/or other threshold). In some embodiments, a minimum vacuum threshold can comprise a threshold of at least −4.4 psi, at least −6 psi, and/or at least −12 psi. In some embodiments, vacuum supply 110 includes or otherwise provides an aspiration reservoir, such as to remove a fluid from locations proximate the distal end of catheter 200 (e.g. gas or other fluid within the GI tract removed in a desufflation procedure and/or a fluid within a distal portion of catheter 200).

In some embodiments, console 100 comprises injectate fluid supply 120. Injectate supply 120 can comprise one or more pumps configured to deliver one or more injectates, injectate 125 shown, to catheter 200 and/or other component of system 10. In some embodiments, injectate supply 120 includes one or more reservoirs configured to store injectate 125. In some embodiments, injectate supply 120 comprise a pump (e.g. a syringe pump configured to drive 1, 2, 3 or more syringes simultaneously or sequentially), such as a pump that is part of pump assembly 195. In some embodiments, injectate supply 120 comprises injectate 125. Injectate supply 120 can deliver fluid to one, two, three or more elements configured to deliver injectate 125 onto and/or into tissue, such as injectate delivery elements 520 described herein. In some embodiments, a single pump (e.g. a single syringe pump) is configured to deliver fluid to two or more injectate delivery elements 520. Injectate supply 120 can be configured to deliver fluid at a flow rate of at least 10 mL/min, such as at a flow rate of at least 15 mL/min, 20 mL/min, 40 mL/min, 60 mL/min, or 120 mL/min. In some embodiments, injectate supply 120 delivers fluid via two or more injectate delivery elements 520 simultaneously (e.g. in a tissue expansion procedure), the fluid delivered at a rate of at least 10 mL/min per injectate delivery element 520, such as at a rate of at least 12.5 mL/min, 15 mL/min, 20 mL/min, 40 mL/min, 60 mL/min, or 120 mL/min per fluid delivery element. In some embodiments, injectate supply 120 is configured to deliver a volume between 2 mL and 20 mL (e.g. approximately 10 mL) to each of multiple injectate delivery elements 520 simultaneously (e.g. two, three or four injectate delivery elements 520 simultaneously), such as a delivery provided in a time period of less than 60 seconds, less than 40 seconds, less than 30 seconds, less than 20 seconds, less than 10 seconds, and/or less than 5 seconds (e.g. in a tissue expansion procedure). Injectate supply 120 can be further configured to deliver fluid (e.g. to injectate delivery elements 520, conduits 521, and/or another component of system 10) at a pressure of at least 40 psi, such as fluid delivered at a pressure of at least 75 psi, 100 psi, 200 psi, or 300 psi. Injectate supply 120 can be configured to provide a bolus of injectate 125 to two, three or more injectate delivery elements 520 (simultaneously or sequentially) in order to expand an axial segment of submucosal tissue (e.g. a full or partial circumferential band of submucosal tissue with a length of at least 0.25 cm, at least 0.5 cm, at least 0.75 cm, at least 1 cm, at least 2 cm, or at least 3 cm), such as to achieve an expansion of the submucosal layer to a thickness (e.g. an expanded thickness) of at least 250 μm, at least 400 μm, or at least 650 μm (e.g. in the area surrounding the volume of mucosal tissue to be subsequently ablated).

Injectate 125 can comprise one or more liquids, gels, and/or other flowable materials ("fluids" herein) for injecting into tissue, such as to expand one or more layers of tissue (e.g. submucosal tissue expanded prior to a mucosal ablation procedure) and/or to narrow a lumen of the intestine and/or other segment of the GI tract (e.g. to create a therapeutic restriction). Alternatively or additionally, injectate 125 can comprise an agent configured to cause tissue necrosis. Alternatively or additionally, injectate 125 can comprise a warming and/or cooling fluid delivered onto and/or into tissue (e.g. a neutralizing fluid such as neutralizing fluid 155 configured to limit, stop and/or at least reduce ablation performed by functional assembly 500). In some embodiments, injectate 125 comprises one, two or more materials selected from the group consisting of: a peptide polymer (e.g. a peptide polymer configured to stimulate fibroblasts to produce collagen); polylactic acid; polymethylmethacrylate (PMMA); a hydrogel; ethylene vinyl alcohol (EVOH); a material configured to polymerize EVOH; dimethyl sulfoxide (DMSO); saline; material harvested from a mammalian body; autologous material; fat cells; collagen; autologous collagen; bovine collagen; porcine collagen; bioengineered human collagen; dermis; a dermal filler; hyaluronic acid; conjugated hyaluronic acid; calcium hydroxylapatite; fibroblasts; a sclerosant; an adhesive; cyanoacrylate; a pharmaceutical agent; a visualizable material; a radiopaque material; a visible dye; ultrasonically reflective material; a combination of materials configured to cause an endothermic reaction when mixed (e.g. when mixed in tissue); a combination of materials configured to cause an exothermic reaction when mixed (e.g. when mixed in tissue); a combination of material configured to expand when mixed (e.g. when mixed in tissue); and combinations of one or more of these. In some embodiments, injectate 125 comprises beads (e.g. pyrolytic carbon-coated beads) suspended in a carrier (e.g. a water-based carrier gel). In some embodiments, injectate 125 comprises a solid silicone elastomer (e.g. heat-vulcanized polydimethylsiloxane) suspended in a carrier, such as a bio-excretable polyvinylpyrrolidone (PVP) carrier gel. In some embodiments, injectate 125 has an adjustable degradation rate, such as an injectate 125 comprising one or more cross linkers in combination with polyalkyleneimines at specific concentrations that result in hydrogels with adjustable degradation properties. In some embodiments, injectate 125 and/or agent 80 (e.g. as described herein) comprises living cells, such as living cells injected into the mucosa or submucosa of the intestine to provide a therapeutic benefit.

In some embodiments, injectate 125 comprises a visualizable and/or otherwise detectable (e.g. magnetic) material (e.g. in addition to one or more materials of above) selected from the group consisting of: a dye; a visible dye; indigo carmine; methylene blue; India ink; SPOT™ dye; a visualizable media; radiopaque material; radiopaque powder; tantalum; tantalum powder; ultrasonically reflective material; magnetic material; ferrous material; and combinations of one or more of these.

In some embodiments, a volume of injectate 125 is delivered into tissue to create a therapeutic restriction (e.g. a therapeutic restriction with an axial length between 1 mm and 20 mm), as described herein, and/or as is described in applicant's co-pending U.S. patent application Ser. No. 17/095,108, entitled "Systems, Devices and Methods for the Creation of a Therapeutic Restriction in the Gastrointestinal Tract", filed Nov. 11, 2020. In some embodiments, a volume of injectate 125 is delivered into tissue to create a safety margin of tissue prior to an ablation procedure configured to ablate target tissue, as is described herein.

In some embodiments, injectate 125 comprises a fluorescent-labeled material or other biomarker configured to identify the presence of a biological substance, such as to identify diseased tissue and/or other tissue for treatment by functional assembly 500 (e.g. to identify target tissue). For example, injectate 125 can comprise a material configured to be identified by imaging device 70 (described below), such as to identify a visualizable change to injectate 125 that occurs after contacting one or more biological substances. In these embodiments, imaging device 70 can comprise a molecular imaging device, such as when imaging device 70 comprises a molecular imaging probe and injectate 125 comprises an associated molecular imaging contrast agent. In these embodiments, injectate 125 can be configured to identify diseased tissue and/or to identify a particular level of one or more of pH, tissue oxygenation, blood flow, and the like. Injectate 125 can be configured to be delivered onto an inner surface of intestinal or other tissue, and/or to be delivered into tissue (i.e. beneath a tissue surface).

In some embodiments, console 100 comprises inflation fluid supply 130. Inflation fluid supply 130 can comprise one or more pumps configured to deliver one or more fluids, inflation fluid 135 shown, to inflate one or more portions of catheter 200 and/or other component of system 10. In some embodiments, inflation fluid supply 130 includes one or more reservoirs configured to store inflation fluid 135. In some embodiments, inflation fluid supply 130 comprises inflation fluid 135. Inflation fluid supply 130 can deliver inflation fluid 135 to a balloon or other reservoir (e.g. other fluid expandable component), such as expandable element 530 described herein. Inflation fluid supply 130 can be configured to deliver a bolus volume of fluid to expandable element 530, such as a bolus of between 0.1 mL and 12 mL, such as an operator selectable bolus volume of 6 mL, 8 mL, and/or 10 mL. Inflation fluid supply 130 can be configured to deliver fluid to expandable element 530 at a pressure of between 0.1 psi and 5 psi. In some embodiments, inflation fluid supply 130 delivers fluid to expandable element 530 prior to a tissue expansion procedure as described herein, in which a separate fluid, e.g. injectate 125, is delivered directly into submucosal or other tissue via one, two or more injectate delivery elements 520. In these embodiments, the fluid provided to expandable element 530 by inflation fluid supply 130 can comprise inflation fluid 135 and/or a different fluid, such as neutralizing fluid 155. Neutralizing fluid 155 can be delivered to expandable element 530 in a submucosal expansion procedure, such as to provide the additional function of pre-cooling or pre-warming tissue proximate element 530 prior to a subsequent thermal ablation procedure (e.g. a heat ablation or cryogenic ablation, respectively, performed by element 530). Alternatively or additionally, inflation fluid supply 130 can deliver neutralizing fluid 155 to element 530 in a tissue expansion procedure performed shortly after a (previous) ablation procedure, such as to perform a post-cooling and/or post-warming of tissue configured to limit the effects of a heat ablation or cryogenic ablation, respectively. For example, pre or post-cooling, and/or pre or post-warming can be performed to reduce time in a previous and/or a subsequent ablation step.

In some embodiments, console 100 comprises ablative fluid supply 140. Ablative fluid supply 140 can comprise one or more pumps configured to deliver one or more ablative fluids, ablative fluid 145 shown, to one or more portions of catheter 200 and/or other component of system 10. In some embodiments, ablative fluid supply 140 includes one or more reservoirs configured to store ablative fluid 145. In some embodiments, ablative fluid supply 140 comprises ablative fluid 145. Ablative fluid supply 140 can deliver ablative fluid 145 to a balloon and/or other fluid storing assembly and/or component of catheter 200, such as an ablative fluid reservoir (e.g. a balloon), expandable element 540 and/or another expandable element 530 described herein. Alternatively or additionally, ablative fluid supply 140 can deliver ablative fluid 145 to one, two, three or more fluid delivery elements configured to deliver fluid onto and/or within tissue, such as injectate delivery elements 520 described herein. Ablative fluid supply 140 can be configured to deliver ablative fluid at a flow rate of at least 5 mL/s, such as at least 8 mL/s, 9 mL/s, 10 mL/s, 15 mL/s, and/or 20 mL/s. In some embodiments, catheter 200 comprises a hydraulic inflow resistance (resistance to ablative fluid supply 140 and/or another fluid supply described herein) of less than 0.05 psi/(mL/min), such as less than 0.036 psi/(mL/min) (e.g. when measured at 85° C. at a flow rate of 570 mL/min). In some embodiments, catheter 200 comprises a hydraulic inflow resistance of at least 0.020 psi/(mL/min), such as at least 0.030 psi/(mL/min) (e.g. when measured at 85° C. at a flow rate of 570 mL/min). In some embodiments, catheter 200 comprises a hydraulic outflow resistance less than 0.070 psi/(mL/min), such as less than 0.63 psi/(mL/min) (e.g. when measured at 85° C. at a flow rate of 570 mL/min). In some embodiments, catheter 200 comprises a hydraulic outflow resistance of at least 0.040 psi/(mL/min), such as at least 0.53 psi/(mL/min) (e.g. when measured at 85° C. at a flow rate of 570 mL/min). Additionally or alternatively, ablative fluid supply 140 can be configured to deliver ablative fluid at a pressure of approximately 40 psi (pressure leaving console 100), such that the pressure of the ablative fluid within expandable element 530 is approximately 20 psi. In some embodiments, ablative fluid supply 140 provides fluid at an ablative temperature (e.g. sufficiently hot or sufficiently cold temperature) in a recirculating manner.

In some embodiments, catheter 200 comprises an inflow pressure drop (e.g. a pressure drop due to flow resistance) of between 17 psi and 21 psi, such as when tested with a flow rate of 10 mL/s of water at 80° C. Additionally or alternatively, catheter 200 can comprise an inflow pressure drop of between 21 psi and 25 psi, such as when tested with a flow rate of 10 mL/s of water at 20° C. In some embodiments, the inflow pressure drop is no more than 50 psi, such as no more than 30 psi, such as no more than 20.5 psi. In some embodiments, the inflow pressure drop is at least 0.5 psi, such as at least 1 psi, such as at least 5 psi, such as at least 15 psi. In some embodiments, catheter 200 comprises a total pressure drop (e.g. a pressure drop due to the flow resistance throughout the entire fluid path) of between 30 psi and 40 psi, such as when tested with a flow rate of 10 mL/s of water at 80° C. Additionally or alternatively, catheter 200 can comprise a total pressure drop of between 39 psi and 50 psi, such as when tested with a flow rate of 10 mL/s of water at 20° C. In some embodiments the total inflow pressure drop is no more than 80 psi, such as no more than 60 psi, such as no more than 50 psi. In some embodiments, the total pressure drop is at least 1 psi, such as at least 5 psi, such as at least 15 psi, such as at least 30 psi, such as at least 35 psi.

In some embodiments, console 100 comprises neutralizing fluid supply 150. Neutralizing fluid supply 150 can comprise one or more pumps configured to deliver one or more neutralizing fluids, neutralizing fluid 155 shown, to one or more portions of catheter 200 and/or other component of system 10 (e.g. a fluid configured to neutralize ablative effects of an ablative fluid delivered by ablative fluid supply 140). In some embodiments, neutralizing fluid supply 150 includes one or more reservoirs configured to store neutralizing fluid 155. In some embodiments, neutralizing fluid supply 150 comprises neutralizing fluid 155. Neutralizing fluid supply 150 can deliver neutralizing fluid 155 to a balloon and/or other fluid storing assembly or component of catheter 200, such as a neutralizing fluid reservoir, expandable element 550, expandable element 540, and/or other expandable element 530 described herein. Alternatively or additionally, neutralizing fluid supply 150 can deliver neutralizing fluid 155 to one, two, three or more fluid delivery elements configured to deliver fluid onto and/or within tissue, such as injectate delivery elements 520 described herein. Neutralizing fluid supply 150 can be configured to deliver neutralizing fluid at a flow rate of at least 5 mL/s, such as at least 8 mL/s, 9 mL/s, 10 mL/s, 15 mL/s, or 20 mL/s. Additionally or alternatively, neutralizing fluid supply 150 can be configured to deliver neutralizing fluid at a pressure of approximately 40 psi (pressure leaving console 100), such that the pressure of the neutralizing fluid within expandable element 530 is approximately 20 psi. In some embodiments, neutralizing fluid supply 150 is configured to deliver neutralizing fluid 155 at a pressure of between 20 psi and 60 psi, such as between 30 psi and 50 psi. In some embodiments, neutralizing fluid 155 pressure is delivered at less than 100 psi. In some embodiments, ablative fluid 145 provided by ablative fluid supply 140 is delivered to a fluid storing component of catheter 200 (e.g. expandable element 530) and neutralizing fluid 155 provided by neutralizing fluid supply 150 is delivered onto and/or within tissue (e.g. via one or more injectate delivery elements 520). Alternatively or additionally, ablative fluid 145 provided by ablative fluid supply 140 can be delivered onto and/or within tissue (e.g. via one or more injectate delivery elements 520), while neutralizing fluid 155 provided by neutralizing fluid supply 150 is delivered to a balloon and/or other fluid storing assembly or component of catheter 200, such as expandable element 530, expandable element 540, and/or expandable element 550 described herein. In some embodiments, ablative fluid supply 140 comprises neutralizing fluid supply 150 (e.g. a single assembly comprising one or more pumps that provide both ablative fluid 145 and neutralizing fluid 155 from one, two or more reservoirs).

In some embodiments, inflation fluid supply 130, ablative fluid supply 140, neutralizing fluid supply 150 and/or another fluid delivery assembly of console 100 is configured to provide fluid (e.g. inflation fluid 135, ablative fluid 145 and/or neutralizing fluid 155) to functional assembly 500 (e.g. to one or more expandable elements 530) at a flow rate of at least 2 mL/sec, such as at least 5 mL/sec, or at a flow rate of approximately 9.5 mL/sec. In some embodiments, console 100 provides fluid to functional assembly 500 at a flow rate of no more than 30 mL/sec.

In some embodiments, console 100 comprises fluid removal pump 160. Fluid removal pump 160 can comprise one or more pumps configured to remove fluid from one or more portions of catheter 200 or other component of system 10. In some embodiments, fluid removal pump 160 includes one or more reservoirs configured to store the one or more removed fluids. In some embodiments, fluid removed by fluid removal pump 160 is recirculated to one or more other assemblies of console 100, such as inflation fluid supply 130, ablative fluid supply 140, neutralizing fluid supply 150, insufflation supply 170 (described herein) and/or functional fluid supply 180 (also described herein). Fluid removal pump 160 can remove fluid from a balloon or other fluid storing assembly or component of catheter 200, such as expandable element 530, expandable element 540, and/or expandable element 550 described herein. In some embodiments, fluid removal pump 160 is configured to remove (e.g. from catheter 200 and/or any component of system 10) injectate 125, inflation fluid 135, ablative fluid 145, neutralizing fluid 155, insufflation fluid 175, and/or functional fluid 185, each as described herein. In some embodiments, catheter 200 comprises a hydraulic outflow resistance as described herein in reference to ablation fluid supply 140. In some embodiments, ablative fluid supply 140 and/or neutralizing fluid supply 150 comprise fluid removal pump 160. In some embodiments, pump assembly 195 comprises fluid removal pump 160.

In some embodiments, console 100 comprises insufflation supply 170. Insufflation supply 170 can comprise one or more pumps configured to deliver a gas or other insufflation fluid, insufflation fluid 175 shown, to inflate the duodenum or other segment of the patient's GI tract. Alternatively or additionally, insufflation supply 170 can be configured to remove insufflation fluid 175 and/or other fluid from the duodenum or other segment of the patient's GI tract (i.e. perform a desufflation). In some embodiments, insufflation supply 170 includes one or more reservoirs configured to store insufflation fluid 175 (to be provided and/or recently removed). In some embodiments, insufflation supply 170 comprises insufflation fluid 175. Insufflation supply 170 can deliver and/or remove fluids via catheter 200 and/or a separate component of system 10, such as an endoscope or other body access device, endoscope 50.

In some embodiments, console 100 comprises functional fluid supply 180. Functional fluid supply 180 can provide functional fluid 185 to one or more components or assemblies of catheter 200 and/or other component of system 10. In some embodiments, functional fluid 185 comprises a hydraulic or pneumatic fluid ("hydraulic fluid" herein). In some embodiments, functional fluid 185 comprises a conductive fluid, such as a fluid configured to transmit electrical power and/or electrical signals between functional assembly 500 and console 100.

As described herein, console 100 can comprise one or more pumps, pump assembly 195. Pump assembly 195 can be configured to deliver and/or extract fluids from catheter 200 (e.g. with or without an intermediate connection device such as umbilical 600 described herein). In some embodiments, pump assembly 195 is fluidly attached to at least injectate supply 120 and/or inflation supply 130, such as to supply injectate 125 and/or inflation fluid 135, respectively, to catheter 200. In some embodiments, pump assembly 195 is fluidly attached to injectate supply 120, inflation fluid supply 130, ablative fluid supply 140, neutralizing fluid supply 150, insufflation supply 170, and/or functional fluid supply 180, such as to deliver and/or remove their associated fluids to and/or from catheter 200. In some embodiments, one or more of injectate supply 120, inflation fluid supply 130, ablative fluid supply 140, neutralizing fluid supply 150, insufflation supply 170, and/or functional fluid supply 180 comprise one or more pumps integrated into their assembly (e.g. one or more pumps of pump assembly 195 are integrated into the supply). In some embodiments, pump assembly 195 is configured as described herebelow in reference to FIG. 1A.

Console 100 comprises one or connectors, connector 102 shown, which fluidly connects to one or more of assemblies 110, 120, 130, 140, 150, 160, 170, and/or 180 of console 100 described herein, via conduits 111, 121, 131, 141, 151, 161, 171, and/or 181, respectively. In some embodiments, console 100 comprises pump assembly 195, which fluidly connects conduits 111, 121, 131, 141, 151, 161, 171, and/or 181 to connector 102 via one or more other conduits, such as conduit 191 shown. Alternatively or additionally, console 100 can comprise one or more manifolds, manifold 700*a* shown, which fluidly connects conduits 111, 121, 131, 141, 151, 161, 171, and/or 181 to connector 102 via one or more other conduits, such as conduit 191 shown. Alternatively, conduits 111, 121, 131, 141, 151, 161, 171, and/or 181 directly attach to connector 102 (i.e. without pump assembly 195 and/or without manifold 700*a*). Manifold 700*a* can be constructed and arranged to fluidly combine one or more of conduits 111, 121, 131, 141, 151, 161, 171 and/or 181. Alternatively or additionally, manifold 700*a* can be constructed and arranged to split (divide) one or more of conduits 111, 121, 131, 141, 151, 161, 171, and/or 181 into multiple conduits. In some embodiments, manifold 700*a* includes one or more valves configured to control flow of fluid in a conduit. In some embodiments, manifold 700*a* includes one or more sensors (e.g. temperature and/or pressure sensors) configured to provide a signal related to a parameter (e.g. temperature and/or pressure) of fluid within a conduit.

In some embodiments, system 10 comprises a connecting device, umbilical 600 which operably connects (e.g. at least fluidly connects) catheter 200 to console 100. Alternatively or additionally, catheter 200 can attach directly to console 100 (e.g. connector 102 of console 100 attaches directly to connector 302 of catheter 200). Umbilical 600 comprises one or more proximal connectors, connector 602*a* shown, which operably attaches to mating connector 102 of console 100. Umbilical 600 comprises one or more distal connectors, connector 602*b* shown, which operably attaches to mating connector 302 of handle assembly 300 of catheter 200. Umbilical 600 can comprise one or more fluid delivery tubes or other fluid-transporting conduits, conduit 691 shown. Conduit 691 comprises one or more lumens or other conduits configured to allow passage of one or more similar and/or dissimilar fluids between console 100 and catheter 200. Each conduit can be configured to receive one or more shafts or other conduits which transport one or more fluids. In some embodiments, umbilical 600 further comprises one or more of: wires or other electrical filaments configured to transmit electrical power and/or signals; optical fibers or other conduits configured to transmit optical power and/or signals; waveguides or other sound conduits configured to transmit sonic power and/or signals; mechanical linkages (e.g. translatable rods); and/or other elongate structures configured to transmit energy, signals, and/or mechanical motion between console 100 and catheter 200. In some embodiments, umbilical 600 comprises one or more sensors, transducers, and/or other functional elements, such as functional element 699 described herein. Functional element 699 can be positioned proximate conduit 691 as shown, positioned proximate connector 602*a*, and/or positioned proximate connector 602*b*.

Catheter 200, including distal portion 208 and distal end 209, comprises handle assembly 300, shaft assembly 400, and functional assembly 500. Handle assembly 300 is positioned on the proximal end or at least a proximal portion of shaft assembly 400, and functional assembly 500 is positioned on catheter 200 distal portion 208 (e.g. on the distal end or at least a distal portion of shaft assembly 400).

Shaft assembly 400 includes at least one elongate shaft, shaft 401, which comprises one or more lumens or other conduits, conduit 491, each of which can be configured to attach to one or more conduits of handle 300, conduit 391. In some embodiments, one or more conduits of conduit 491 simply passes through handle 300 (e.g. to operably attach to umbilical 600 and/or console 100). Each conduit of shaft 401 can be configured to transport fluid and/or it can be sized to receive (e.g. slidingly receive) one or more separate shafts, such as one or more shafts that transport fluid. In some embodiments, on or more lumens of shaft 401 receive a separate shaft, and fluid is transported within the received shaft and/or between the outer diameter of the received shaft and the wall of the lumen of shaft 401, such as is described herein. Alternatively or additionally, each lumen of shaft 401 and/or one or more shafts inserted within the lumen can surround (e.g. slidingly or fixedly surround) one or more conduits configured to transmit energy, signals, and/or mechanical motion between console 100 and catheter 200, as described herein. In some embodiments one or more conduits 491 are fixedly attached within shaft 401 with adhesive, such as with one or more rings of adhesive positioned about the outer wall of a conduit 491 and a surrounding wall (e.g. the inner wall of a sleeve, lumen, or other tube) onto which conduit 491 is to be fixedly attached. For example, two or more rings of adhesive can be positioned between the outer wall of a conduit 491 and a surrounding wall (e.g. a surrounding wall of a sleeve) to prevent undesired translation of the conduit 491.

Shaft assembly 400 comprises proximal end 405, proximal portion 406, middle portion 407, distal portion 408, and distal end 409. Distal portion 408 is shown in a magnified view. Positioned on distal portion 408 is functional assembly 500, configured as a treatment assembly and/or diagnostic assembly (e.g. an assembly configured to treat and/or diagnose tissue of the intestine or other GI tract tissue). In some embodiments, shaft 401 extends through and beyond functional assembly 500 (as shown in FIG. 1, where catheter 200 distal end 209 is the same as shaft assembly 400 distal end 409). Alternatively, functional assembly 500 can be positioned on the distal end of shaft 401. In some embodiments, shaft 401 comprises a twist, such as is described herebelow in reference to FIG. 4. In some embodiments, shaft 401 comprises a bulbous tip. In some embodiments, shaft 401 comprises a tapered tip, such as is described herebelow in reference to FIGS. 3A and 3B.

In some embodiments, shaft assembly 400 comprises a lumen to slidingly receive a guidewire, such as a passageway including a lumen which exits at a location proximate the distal end 409 of shaft assembly 400 at an opening, port 490. In some embodiments, shaft assembly 400 comprises one or more lumens for performing insufflation and/or desufflation ("insufflation" herein), such as conduit 571 comprising one or more lumens which terminate in one or more openings, such as port 470D positioned distal to functional assembly 500 and port 470*p* positioned proximal to functional assembly 500, each as shown and described herein. In some embodiments, port 470*p* and/or port 470D is configured to perform desufflation only, or insufflation only.

In some embodiments, shaft assembly 400 comprises one or more manifolds, manifold 700*c* and/or 700*d* shown, which fluidly connects one or more conduits of conduit 491 to one or more other conduits (e.g. one or more other conduits of conduit 491 or one or more other conduits of catheter 200). Manifolds 700*c* and/or 700*d* can be constructed and arranged to fluidly combine one or more of lumens of conduit 491. Alternatively or additionally, manifolds 700*c* and/or 700*d* can be constructed and arranged to split (divide) one or more of lumens of conduit 491 into multiple lumens. In some embodiments, manifolds 700*c* and/or 700*d* includes one or more valves (e.g. one or more one-way valves) configured to control flow of fluid in a conduit. In some embodiments, manifolds 700*c* and/or 700*d* includes one or more sensors (e.g. temperature and/or pressure sensors) configured to provide a signal related to a parameter (e.g. temperature and/or pressure) of fluid within a conduit.

In some embodiments, shaft assembly 400 comprises one or more sensors, transducers, and/or other functional elements, such as functional element 499*a* (e.g. positioned in a mid-portion of shaft 401 and/or proximate manifold 700*c*) and/or functional element 499*b* (e.g. positioned proximate manifold 700*d* and/or functional assembly 500) as shown and described herein. In some embodiments, functional element 499*a* and/or 499*b* comprises a radiopaque marker and/or other visualizable marker, as described herein, configured to allow an operator to visualize translation and/or rotation of shaft assembly 400 (e.g. to visualize translation and/or rotation of functional assembly 500), such as via imaging device 70 (e.g. a fluoroscope or other imaging device).

Shaft 401 can comprise a length of at least 60", such as at least 72". In some embodiments, shaft 401 comprises an outer diameter of less than 0.3", such as a diameter less than 0.256", 0.1", or 0.08". Shaft 401 can comprise a material selected from the group consisting of: a polyether block amide such as Pebax™; a thermoplastic elastomer, such as Tygon™, Arnitel™, or Hytrel™; and combinations of one or more of these. In some embodiments, at least a portion of shaft 401 comprises a radiopaque additive, such as barium sulfate. In some embodiments, at least a portion of shaft 401 comprises a lubricious coating or additive, such as Propell™ low friction compound manufactured by Foster Corporation of Putnam, CT In some embodiments, at least a portion of shaft 401 comprises a heat stabilizer, a light stabilizer, and/or other stabilizing agent, such as an HLS™ heat and light stabilizer manufactured by the Foster Corporation of Putnam, CT.

Functional assembly 500 comprises one or more assemblies configured to treat and/or diagnose tissue. In some embodiments, functional assembly 500 is configured to both treat and diagnose tissue. Functional assembly 500 can be configured to treat and/or diagnose duodenal tissue or other tissue of the GI tract. Functional assembly 500 can be positioned on distal portion 408 of shaft assembly 400 as shown. Functional assembly 500 can be configured to radially expand and/or radially contract, such as when functional assembly comprises one or more expandable reservoirs, such as one or more of expandable elements 530, 540 and/or 550 shown (singly or collectively, expandable element 530). Each expandable element 530, 540 and/or 550 (singly or collectively expandable element 530) can comprise a balloon or other expandable reservoir ("balloon" herein), an expandable cage, a furlable element, and the like. Expandable element 530 can comprise one or more balloons that circumferentially surround shaft 401 (e.g. in a linear arrangement), or multiple partially circumferential balloons (e.g. in a radial arrangement). Expandable elements 530 can comprise one or more balloons that expand radially out from shaft 401, at the same or different axial locations along shaft 401. An expandable element 530 can comprise an array of balloons in a lobed configuration, circumferentially spaced. An expandable element 530 can comprise one or more inner balloons surrounded by one or more outer balloons (e.g. where the inner balloon receives a first fluid at a first temperature and the space between the inner and outer balloons receives a second fluid at a second temperature, different than the first temperature). Expandable element 530 can comprise a balloon or other element configured to expand to a diameter of less than or equal to 35 mm, such as less than or equal to 30 mm or 25 mm. Expandable element 530 can comprise a material as described herein. Expandable element 530 can comprise a balloon with a wall thickness as described herein. In some embodiments, one or more portions of expandable element 530 comprise a non-compliant material and one or more other portions of expandable element 530 comprises a compliant material. In some embodiments, expandable element 530 is configured to withstand an inflation pressure of up to 50 psi, such as up to 60 psi, 100 psi, or 200 psi. In some embodiments, a first expandable element 530 comprises at least a portion comprising a non-compliant material and a second expandable element 540 comprises at least a portion comprising a compliant material.

Functional assembly 500 can comprise one or more balloons configured to receive one or more fluids, such as an expandable element 540 configured to receive an ablative fluid (e.g. a fluid at an ablative temperature received from ablative fluid supply 140), an expandable element 550 configured to receive a neutralizing fluid (e.g. a fluid received from neutralizing fluid supply 150 and comprising a temperature configured to cool or warm tissue after a heat or cryogenic ablation, respectively), or other expandable element 530. In some embodiments, at least expandable element 540 and expandable element 550 are the same reservoir (e.g. the same one or more balloons) that receive both ablative fluid and neutralizing fluid.

In some embodiments, functional assembly 500 is configured to expand one or more layers of tissue, such as to expand one or more layers of submucosal tissue prior to a tissue treatment procedure in which a mucosal layer of tissue is treated (e.g. thermally or chemically ablated). In these embodiments, functional assembly 500, catheter 200 and/or any component of system 10 can be of similar construction and arrangement to that described in: applicant's co-pending U.S. patent application Ser. No. 14/515,324, entitled "Tissue Expansion Devices, Systems and Methods", filed Oct. 15, 2014; applicant's co-pending U.S. patent application Ser. No. 17/095,108, entitled "Systems, Devices and Methods for the Creation of a Therapeutic Restriction in the Gastrointestinal Tract", filed Nov. 11, 2020; and applicant's co-pending U.S. patent application Ser. No. 17/110,720, entitled "Injectate Delivery Devices, Systems and Methods", filed Dec. 3, 2020.

In some embodiments, functional assembly 500 is configured to receive an ablative fluid (e.g. a recirculating hot or cold fluid at a tissue-ablating temperature) to treat tissue. In some embodiments, functional assembly 500 is configured to deliver an ablation fluid directly onto tissue (e.g. a hot or cold liquid or gas at a tissue-ablating temperature, and/or a chemically ablative fluid). In these embodiments, functional assembly 500, catheter 200 and/or any component of system 10 can be of similar construction and arrangement to that described in: applicant's co-pending U.S. patent application Ser. No. 16/438,362, entitled "Heat Ablation Systems, Devices and Methods for the Treatment of Tissue", filed Jun. 11, 2019 and applicant's co-pending U.S. patent application Ser. No. 14/917,243, entitled "Systems, Methods and Devices for Treatment of Target Tissue", filed Mar. 7, 2016.

Functional assembly 500 can include one or more ports configured to capture and/or engage tissue (singly or collectively "capture" or "engage" herein) or otherwise stabilize functional assembly 500 within a GI lumen, such as tissue capture chambers 510 shown and described herein. Each tissue capture chamber 510 includes an opening, opening 512. In some embodiments, functional assembly 500 (or another portion of catheter 200) includes two, three, four or more tissue capture chambers 510. Each tissue capture chamber 510 can be attached to a source of vacuum, such as conduit 511 which is fluidly attached to a source of vacuum provided by console 100, such as vacuum supply 110. Each tissue capture chamber 510 can be of similar construction and arrangement to any chamber 510 described herein. In some embodiments, injectate delivery element 520 is positioned above (radially out from) a source of vacuum that is provided to tissue capture chamber 510. In some embodiments, one or more tissue capture chambers 510 is constructed of a metal or other material with a relatively high thermal conductance, such as to efficiently transfer heat from and/or to expandable element 530 (e.g. from and/or to temperature-ablative fluid within expandable element 530), such as to avoid non-ablated tissue regions proximate tissue capture chambers 510.

Functional assembly 500 can comprise one or more elements configured to deliver fluid into tissue, such as injectate delivery elements 520 shown, each positioned within or at least proximate a tissue capture chamber 510. In some embodiments, functional assembly 500 (or another portion of catheter 200) includes two, three, four or more injectate delivery elements 520. Injectate delivery elements 520 can comprise one or more elements selected from the group consisting of: needle; fluid jet; iontophoretic element; and combinations of one or more of these. Each injectate delivery element 520 can be operably attached to one or more conduits of catheter 200, such when fluidly connected to conduit 521 shown or when fluidly attached to a separate conduit slidingly received by conduit 521 as described herein. Each injectate delivery element 520 can be connected to a source of fluid, such as a fluid provided by console 100 via injectate supply 120, ablative fluid supply 140, neutralizing fluid supply 150, and/or functional fluid supply 180. One or more injectate delivery elements 520 can comprise a needle with a diameter between 16 gauge and 34 gauge, such as a needle with a 27 gauge or 29 gauge diameter One or more injectate delivery elements 520 can comprise a needle with a bevel angle of approximately 10° (e.g. with a bevel length of 0.008"), such as a bevel angle of at least 5° and/or a bevel angle no more than 45° or no more than 80°. One or more injectate delivery elements 520 can be advanced into the tissue contained in the associated tissue capture chambers 510, while avoiding the potential of the injectate delivery elements 520 penetrating an outer layer and/or outside of the GI wall tissue (e.g. injectate delivery elements 520 do not exit chambers 510). In some embodiments, tissue is penetrated by a needle-based injectate delivery element 520 at the time of the application of the vacuum to chamber 510, without the advancement of injectate delivery elements 520 (e.g. when the distal end of each injectate delivery element 520 is positioned within the associated chamber 510). In some embodiments, one or more injectate delivery elements 520 comprises a fluid jet, and injectate 125 or other fluid can be delivered into tissue captured within chamber 510 without advancement of the fluid jet. Each tissue capture chamber 510 can be configured to slidingly receive an injectate delivery element 520 (e.g. at a time in which tissue is captured within chamber 510 and the injectate delivery element 520 penetrates the captured tissue upon advancement), such as when a tissue capture chamber 510 is configured to slidingly receive at least a 29 gauge needle, or at least a 27 gauge needle. Each injectate delivery element 520 can be configured to be advanced a distance of at least 2.5 mm, at least 3.5 mm, or at least 4.5 mm. Each tissue capture chamber 510 can comprise a width of at least 0.010", at least 0.040" or at least 0.060". Each tissue capture chamber 510 can comprise a width of no more than 0.25", or no more than 0.35". Each tissue capture chamber 510 can comprise a length of at least 0.010", at least 0.040" at least 0.060", at least 0.090", or at least 0.120". Each tissue capture chamber 510 can comprise a length of no more than 0.9", no more than 0.7", or no more than 0.5". Each tissue capture chamber 510 can comprise a depth of at least 300 μm, at least 500 μm, at least 700 μm, or at least 1000 μm. Each tissue capture chamber 510 can comprise a depth of no more than 2500 μm, such as no more than 2000 μm.

In some embodiments, one or more of tissue capture chambers 510 each include a functional element 599 comprising one, two, or more springs configured to bias injectate delivery element 520 in an advanced position. Alternatively or additionally, chambers 510 can each include a functional element 599 comprises one, two, or more springs configured to bias the injectate delivery elements 520 in the retracted position. In some embodiments, catheter 200 includes a functional element 599 comprising one or more linkages each operably attached to an injectate delivery element 520. The one or more linkages can be operably attached to one or more controls of handle 300, such that an operator of system 10 can manipulate the position of the one or more injectate delivery elements 520 via handle 300 (e.g. by translating the linkages). In some embodiments, injectate delivery elements 520 are configured to be advanced and/or retracted within tissue capture chambers 510 via hydraulic pressure. For example, one or more injectate delivery elements 520 can be configured to be advanced by the hydraulic pressure of injectate 125 being delivered via injectate delivery element 520. In these embodiments, injectate delivery element 520 can be biased in a retracted position (e.g. via a spring) such that element 520 returns to the retracted position when the hydraulic pressure is removed. In some embodiments, one or more injectate delivery elements 520 can be advanced and/or retraced via magnetic activation and/or deactivation (e.g. via a functional element 599 comprising one or more magnetic elements).

Functional assembly 500 of FIG. 1 can comprise two tissue capture chambers 510 (e.g. separated circumferentially at approximately 180°) or three tissue capture chambers 510 (e.g. separated circumferentially at approximately 120°), and each can surround an injectate delivery element 520. In some embodiments, four or more tissue capture chambers 510 are included. Each tissue capture chamber 510 can be configured to engage with tissue, such as to maintain contact between functional assembly 500 and tissue (e.g. during delivery and/or removal of energy to and/or from tissue). Alternatively or additionally, tissue capture chamber 510 can be configured to capture tissue within tissue capture chamber 510, via application of a vacuum, as described herein, such as to allow delivery of fluid or a fluid delivery element (e.g. a needle) into the captured tissue.

Functional assembly 500 can comprise one or more ports (e.g. openings) in shaft assembly 400 that are configured to deliver fluid into and/or remove fluid from expandable element 530, such as ports 430 and 460 shown. Ports 430 and 460 can be positioned in various locations within expandable element 530. In some embodiments, port 460 is configured to remove fluid from expandable element 530, and is positioned in a proximal portion of functional assembly 500. In some embodiments, port 430 is configured to deliver fluid into expandable element 530, and can be positioned in a distal (as shown), middle or proximal portion of functional assembly 500. Port 430 can comprise one or more openings which are fluidly attached to one or more conduits, such as conduits 531, 541, and/or 551 as shown, which are fluidly connected to one or more of inflation fluid supply 130, ablative fluid supply 140 and/or neutralizing fluid supply 150, respectively, or other fluid supply of console 100 (e.g. functional fluid supply 180). Port 460 can comprise one or more openings fluidly connected to one or more conduits, such as conduit 561 as shown, which is fluidly connected to fluid removal pump 160 of console 100. In some embodiments, port 460 is fluidly attached to conduits 531, 541, and/or 551, which are fluidly connected to one or more of inflation fluid supply 130, ablative fluid supply 140 and/or neutralizing fluid supply 150, respectively, or other fluid supply of console 100 (e.g. functional fluid supply 180).

In some embodiments, functional assembly 500 comprises one or more sensors, transducers, and/or other functional elements, such as functional element 599 shown and described herein. In some embodiments, functional element 599 comprises a radiopaque marker and/or other visualizable marker, as described herein, configured to allow an operator to visualize translation and/or rotation of functional assembly 500, such as via imaging device 70 (e.g. a fluoroscope or other imaging device). In some embodiments, functional element 599 comprises a heat-generating transducer, such as an element comprising one, two, or more electrodes through which radiofrequency (RF) energy is passed, such as to heat expandable element 530, 540, and/or 550, and/or to heat fluid (e.g. saline) contained within expandable element 530, 540, and/or 550. Alternatively or additionally, functional element 599 can comprise a cooling transducer (e.g. a Peltier cooling element), such as to cool expandable element 530, 540, and/or 550, and/or to cool fluid contained within expandable element 530, 540, and/or 550.

Handle assembly 300 comprises a handle for an operator to manipulate catheter 200, including housing 301. Handle assembly 300 can be positioned in proximal end 405 of shaft assembly 400 as shown. Handle assembly 300 comprises one or more conduits, conduit 391. Conduit 391 can be configured to operably attach (e.g. on its proximal end or ends) to connector 102 of console 100 or to conduit 691 of umbilical 600. Conduit 391 is configured to operably attach (e.g. on its distal end or ends) to conduit 491 of shaft assembly 400. In some embodiments, handle assembly 300 comprises a reusable portion and a disposable portion. In some embodiments, handle assembly 300 comprises a reusable handle assembly constructed and arranged to operably connect to a disposable catheter 200 (e.g. a single use catheter). Alternatively or additionally, handle assembly 300 comprises a disposable handle assembly. In some embodiments, catheter 200 comprises one or more reusable portions and one or more disposable portions (e.g. one or more disposable portions configured to operably attach to a reusable portion). For example, one or more conduits of catheter 200 can comprise reusable conduits, such as one or more reusable conduits configured to operably attach to one or more disposable injectate delivery elements 520 (e.g. operably attached prior to a clinical procedure). In some embodiments, handle assembly 300 comprises one or more manifolds, manifold **700*b* shown, which fluidly connects one or more conduits of conduit 391 to one or more other conduits (e.g. one or more other conduits of conduit 391 and/or conduit 491). Manifold 700*b* can be constructed and arranged to fluidly combine one or more of lumens of conduit 391. Alternatively or additionally, manifold 700*b* can be constructed and arranged to split one or more of lumens of conduit 391 into multiple lumens. In some embodiments, manifold 700*b* includes one or more valves configured to control flow of fluid in a conduit. In some embodiments, manifold 700*b*** includes one or more sensors (e.g. temperature and/or pressure sensors) configured to provide a signal related to a parameter (e.g. temperature and/or pressure) of fluid within a conduit.

Handle assembly 300 can include one or more controls, control 310, which can be configured to activate, manipulate and/or otherwise operate one or more functions of catheter 200. In some embodiments control 310 comprises a control for advancing and/or retracting one or more injectate delivery elements 520 (e.g. simultaneously advancing and/or retracting two, three or more injectate delivery elements 520). In some embodiments, control 310 is configured to adjust one or more operating parameters of console 100 (e.g. via a wired or wireless connection). In some embodiments, control 310 comprises a software-enabled control, for example when handle assembly 300 includes a touch screen display configured to display a graphical user interface (GUI) comprising one or more icons for controlling one or more functions of system 10. In some embodiments, functional element 599 comprises a sensor. System 10 can be configured for closed loop control of one or more functions of system 10 based on feedback from the sensor. In some embodiments, system 10 can be configured as a "manual system", where the operator is the primary controller of the actions of the system (e.g. positioning of catheter 200 and/or the advancement of injectate delivery elements 520). Alternatively or additionally, the operator can be assisted by system 10, for example when the operator initiates one or more robotic actions of system 10, thereby controlling the procedure through a series of inputs to system 10 (e.g. inputs via the GUI). For example, system 10 can comprise a robotic system of similar construction and arrangement to similar robotic systems described in applicant's co-pending U.S. Provisional Patent Application Ser. No. 62/961,340, titled "Automated Tissue Treatment Devices, Systems, and Methods", filed Jan. 15, 2020.

Handle assembly 300 can include an entry port, such as port 392, for passage of a guidewire or other filament, such as guidewire 60. In some embodiments, port 392 is positioned on a proximal portion of shaft assembly 400. Port 392 can be operably connected to a lumen of shaft 401, such as is described herein.

In some embodiments, handle assembly 300 comprises one or more sensors, transducers, and/or other functional elements, such as functional element 399 shown and described herein. In some embodiments, functional element 399 comprises a tactile transducer configured to alert an operator of a particular state of catheter 200 (e.g. an alarm or warning state, a "ready" state, a "function completed" state, and the like). For example, functional element 399 can alert an operator that a particular function is being performed, such as a function selected from the group consisting of: heating of tissue is being performed (e.g. via hot fluid present in functional assembly 500); a cooling of tissue is being performed (e.g. via cold fluid present in functional assembly 500); injectate is being delivered into tissue (e.g. injectate 125 is being delivered into submucosal or other tissue via one, two, three or more injectate delivery elements 520); needles or other injectate delivery elements 520 have been advanced into tissue; and combinations of one or more of these. Functional element 399 can comprise a tactile transducer selected from the group consisting of: a vibrational transducer (e.g. a vibrational transducer that alerts an operator that injectate is being delivered into tissue and/or injectate delivery elements 520 are presently advanced into tissue); a heating element (e.g. a heating element that alerts an operator that a heat ablation and/or warming of tissue is in process); a Peltier element or other cooling element (e.g. a cooling element that alerts an operator that a cryogenic ablation and/or cooling of tissue is in process); and combinations of one or more of these. In some embodiments, handle assembly 300 includes a portion configured to alert an operator of one or more particular functional states of catheter 200.

One or more functional elements can be included in system 10, such as functional element 199 of console 100, functional element 399 of handle assembly 300, functional element 499*a* and/or 499*b* of shaft assembly 400, functional element 599 of functional assembly 500, and/or functional element 699 of umbilical 600.

Endoscope 50 can comprise one or more endoscopes configured to reach at least one or more portions of the duodenum from the patient's mouth. In some embodiments, endoscope 50 comprises an endoscope similar to Olympus model number PCF-PH190.

Guidewire 60 can comprise an outside diameter of approximately 0.035". Guidewire 60 can comprise a "stiff" or "super stiff" configuration, such as a guidewire similar to a Jagwire Stiff Straight guidewire, a Wallstent Super Stiff guidewire, a Dreamwire Superstiff, and/or a Savary Gilliard guidewire. Guidewire 60 can comprise a length of at least twice the length of catheter 200 and/or endoscope 50, such that one or more devices can be "exchanged" over guidewire 60. Guidewire 60 can comprise a material selected from the group consisting of: nitinol; stainless steel; and combinations of one or more of these. Guidewire 60 can comprise a hydrophilic or other lubricious coating, such as a Teflon coating.

In some embodiments, system 10 further comprises imaging device 70, which can comprise an imaging device constructed and arranged to provide an image of the patient's anatomy (e.g. inner wall or any part of the intestine of the patient) and/or an image of all or part of catheter 200 or other portion of system 10, as described in detail herein. Imaging device 70 can comprise an imaging device selected from the group consisting of: endoscope camera; visible light camera; infrared camera; X-ray imager; fluoroscope; CT Scanner; MRI; PET Scanner; ultrasound imaging device; molecular imaging device; and combinations of one or more of these. In some embodiments, a patient image is used to set, confirm and/or adjust one or more system 10 parameters, such as when imaging device 70 comprises a sensor of the present inventive concepts configured to produce a signal.

In some embodiments, system 10 further comprises one or more agents, agent 80 shown. Agent 80 can be delivered by one or more components of system 10, such as by endoscope 50 (via one or more working channels of endoscope 50) and/or by catheter 200 (e.g. via one or more injectate delivery elements 520 or ports 470). Agent 80 can comprise a material selected from the group consisting of: anti-peristaltic agent, such as L-menthol (i.e. oil of peppermint); glucagon; buscopan; hyoscine; somatostatin; a diabetic medication; an analgesic agent; an opioid agent; a chemotherapeutic agent; a hormone; and combinations of one or more of these. In some embodiments, agent 80 comprises cells delivered into the intestine, such as living cells delivered into intestinal mucosa or submucosa via one or more injectate delivery elements 520. In some embodiments, agent 80 comprises one or more agents configured to be delivered into expandable element 530 and to pass through at least a portion of expandable element 530 and into the intestine (e.g. when expandable element 530 comprises at least a portion that is porous). In some embodiments, agent 80 comprises a mucolytic agent configured to remove mucus from a tissue surface.

In some embodiments, system 10 comprises a tissue marker, marker 90 shown, which can comprise a dye or other visualizable media configured to mark tissue (e.g. a dye delivered using a needle-based tool, and/or a visualizable temporary implant used to mark tissue, such as a small, temporary anchor configured to be attached to tissue and removed at the end of the procedure or otherwise passed by the natural digestive process of the patient shortly after procedure completion). Marker 90 can be deposited or deployed in reference to (e.g. to allow an operator to identify) non-target tissue (e.g. a marker positioned proximate the ampulla of Vater to be visualized by an operator to avoid damage to the ampulla of Vater), and/or to identify target tissue (e.g. tissue to be ablated). In some embodiments, marker 90 is deposited or deployed in reference to tissue selected from the group consisting of: gastrointestinal adventitia; duodenal adventitia; the tunica serosa; the tunica muscularis; the outermost partial layer of the submucosa; ampulla of Vater; pancreas; bile duct; pylorus; and combinations of one or more of these.

Shaft 401 can comprise at least six lumens, at least eight lumens, or at least ten lumens. In some embodiments, shaft 401 comprises a single shaft comprising the at least six lumens or at least eight lumens. In these embodiments, a first pair of lumens of shaft 401 can be in fluid communication with a first tissue capture chamber 510, a second pair of lumens of shaft 401 can be in fluid communication with a second tissue capture chamber 510; and a third pair of lumens of shaft 401 can be in fluid communication with expandable element 530 (e.g. via openings in shaft 401, ports 430 and 460). The first pair of lumens of shaft 401 can comprise a vacuum lumen and a lumen that slidingly receives a first tube attached to a first injectate delivery element 520. The second pair of lumens of shaft 401 can comprise a vacuum lumen and a lumen that slidingly receives a second tube attached to a second injectate delivery element 520. The third pair of lumens of shaft 401 can comprise a fluid delivery lumen that delivers fluid to expandable element 530 and a fluid removal lumen that removes fluid from expandable element 530 (e.g. via ports 430 and 460, respectively), as described herein. In some embodiments, the at least one flexible elongate shaft comprises at least eight lumens, and a fourth pair of lumens are in fluid communication with a third tissue capture chamber 510. In some embodiments, shaft 401 further comprises, as described herein, one or more of: a guidewire lumen; a first insufflation lumen; and/or a second insufflation lumen. In some embodiments, shaft 401 comprises multiple shafts, such as two shafts 401 that each include at least a pair of lumens, or three shafts 401 that each include at least a pair of lumens.

In some embodiments, shaft 401 comprises a first lumen for delivering fluid to expandable element 530 (e.g. delivering to element 530 one or more of: inflation fluid 135, ablative fluid 145 and/or neutralizing fluid 150), and a second lumen for removing fluid from expandable element 530 (e.g. removing from element 430 one or more of inflation fluid 135, ablative fluid 145 and/or neutralizing fluid 155). In some embodiments, shaft 401 comprises two, three or more lumens configured to provide and remove fluid from expandable element 530 in a recirculating manner.

Expandable element 530, 540 and/or 550 (singly or collectively expandable element 530) can comprise various materials and dimensions that are configured to optimize the performance of one or more functions, such as submucosal tissue expansion (e.g. duodenal submucosal tissue expansion), mucosal tissue treatment (e.g. duodenal mucosal tissue ablation or other treatment), and/or substance delivery (e.g. delivery of one or more substances into the mucosa, submucosa, and/or other luminal wall location of the duodenum, jejunum, ileum, and/or other GI wall location). In some embodiments, expandable element 530 comprises a diameter (e.g. an expanded diameter of a balloon-based expandable element 530) of at least 5 mm and/or of no more than 45 mm, such as a diameter of at least 18 mm and/or of no more than 32 mm, such as a diameter of at least 23.5 mm and/or no more than 26.5 mm, such as a diameter of approximately 24 mm or 25 mm. In some embodiments, expandable element 530 comprises a balloon with a wall thickness (e.g. thickness of a single wall of the balloon) of at least 0.0001 in and/or of no more than 0.01 in, such as a wall thickness of at least 0.00025 in and/or no more than 0.003 in, such as a wall thickness of at least 0.0005 in and/or no more than 0.001 in, such as a wall thickness of approximately 0.00075 in. In some embodiments, expandable element 530 comprises a balloon with varied wall thickness, such as wall thickness that varies and has a thickness of at least 0.00025 in and/or no more than 0.003 in. For example, expandable element 530 can comprise an increased wall thickness proximate tissue capture cambers 510. In some embodiments, expandable element 530 comprises a material selected the group consisting of: a compliant material; a non-compliant material; both a compliant and a non-compliant material; PET; polyimide; nylon; nylon 12; PEEK; a silicone elastomer; polyether block amide; a polyurethane; a thermoplastic elastomer; and combinations thereof. In some embodiments, expandable element 530 (e.g. a balloon-based expandable element 530) comprises a compliance of at least 0.0001% and/or no more than 200%, such as a compliance of at least 0.0001% and/or no more than 15%, such as a compliance between at least 0.0001% and/or no more than 8%. In some embodiments, expandable element 530 comprises one or more materials with a thermal conductivity (W/(m*K)) of at least 0.01 and/or nor more than 10, such as a thermal conductivity of at least 0.1 and/or no more than 0.6, such as a thermal conductivity of approximately 0.29. In some embodiments, expandable element 530 comprises a contact length (e.g. a length of expandable element 530 in contact with duodenal or other luminal wall tissue when inflated or otherwise expanded) of at least 5 mm and/or no more than 500 mm, such as a contact length of at least 10 mm and/or no more than 50 mm, such as a contact length of at least 19 mm and/or no more than 21 mm, such as a contact length of approximately 20 mm. In some embodiments, expandable element 530 (e.g. an inflated balloon-based expandable element 530) comprises a tapered proximal and/or distal end, such as a tapered end with a taper angle (e.g. a proximal and/or distal taper angle) of at least 5° and/or no more than 120°, such as a taper angle of at least 30° and/or no more than 90°, such as a taper angle of at least 57° and/or no more than 63°, such as a taper angle of approximately 60°. Expandable element 530 can comprise proximal and distal tapers that are similar or dissimilar. In some embodiments, expandable element 530 comprises a balloon which includes a braid on and/or within its wall, such as a metal braid and/or non-metal braid (e.g. a nylon braid).

Injectate delivery elements 520 can comprise one or more needles or other fluid delivery elements as described herein. Injectate delivery elements 520 can comprise one or more needles or other fluid delivery elements that are configured to deliver fluid or other material to tissue to perform one or more functions, such as submucosal tissue expansion (e.g. duodenal submucosal tissue expansion), mucosal tissue treatment (e.g. duodenal mucosal tissue ablation or other treatment), and/or substance delivery (e.g. delivery of one or more substances into the mucosa, submucosa, and/or other luminal wall location of the duodenum, jejunum, ileum, and/or other GI wall location). In some embodiments, injectate delivery elements 520 comprise elements (e.g. needles) constructed of a material selected from the group consisting of: metal; stainless steel, plastic; PEEK, liquid crystal polymer; and combinations of these. In some embodiments, injectate delivery element 520 comprises one or more needles with an inner diameter of at least 0.0014 in and/or no more than 0.033 in, such as an inner diameter of at least 0.00625 in and/or no more than 0.01325 in, such as an inner diameter of at least 0.0075 in and/or no more than 0.009 in, such as an inner diameter of approximately 0.008 in. In some embodiments, injectate delivery element 520 comprises one or more needles constructed and arranged to have an exposed length of at least 0.125 mm and/or no more than 10 mm, such as an exposed length of at least 1 mm and/or no more than 5 mm, such as an exposed length of at least 2 mm and/or no more than 3 mm, such as an exposed length of approximately 2.5 mm. In some embodiments, injectate delivery element 520 comprises one or more needles with a diameter (e.g. Birmingham gauge) of at least 36 gauge and/or no more than 10 gauge, such as a gauge of at least 35 and/or no more than 20, such as a gauge of at least 27 and/or no more than 26. In some embodiments, injectate delivery element 520 comprises one or more needles with a bevel angle of at least 1° and/or no more than 90°, such as a bevel angle of at least 5° and/or no more than 45°, such as a bevel angle of at least 9° and/or no more than 11°, such as a bevel angle of approximately 10°.

Console 100 can comprise one or more fluid supplies, as described herein, such as to deliver fluid to one or more injectate delivery elements 520. In some embodiments, console 100 is configured (e.g. during a submucosal tissue expansion procedure) to provide fluid to each injectate delivery element 520 at a flow rate of at least 0.1 mL/min and/or no more than 120 mL/min, such as a flow rate of at least 1 mL/min and/or no more than 60 mL/min, such as a flow rate of at least 5 mL/min and/or no more than 20 mL/min, such as a flow rate of approximately 12.5 mL/min. In some embodiments, console 100 is configured (e.g. during a submucosal tissue expansion procedure) to provide, to each injectate delivery element 520, an injection volume (e.g. for delivery at each injection site) of at least 0.1 mL and/or no more than 100 mL, such as an injection volume of at least 1 mL and/or no more than 30 mL, such as an injection volume of at least 8 mL and/or no more than 12 mL, such as an injection volume of at least 9 mL and/or no more than 11 mL, such as an injection volume of approximately 10 mL. In some embodiments, console 100 is configured to provide fluid, to each injectate delivery element 520 (e.g. during a submucosal tissue expansion procedure), at a pressure of at least 1 psi and/or no more than 400 psi, such as at a pressure of at least 20 psi and/or no more than 200 psi, such as at a pressure of at least 90 psi and/or no more than 110 psi, such as at a pressure of approximately 100 psi.

Catheter 200 can comprise multiple fluid-carrying conduits as described herein. For example, multiple conduits 521, also described herein, can each attach to a fluid delivery element 520 and travel to the proximal end or at least a proximal portion of catheter 200 (e.g. conduits 521 positioned within shaft 501 and fluidly attached to a port of handle assembly 300). In some embodiments, one or more conduits 521 comprises an inner diameter of at least 0.005 in and/or no more than 0.125 in, such as an inner diameter of at least 0.04 in and/or no more than 0.10 in, such as an inner diameter of at least 0.0177 in and/or no more than 0.0183 in, such as an inner diameter of approximately 0.018 in. In some embodiments, one or more conduits 521 each comprises a length of at least 12 in and/or no more than 250 in, such as a length of at least 36 in and/or no more than 120 in, such as a length of approximately 78 in.

Functional assembly 500 can comprise one, two, three, or more tissue capture chambers 510, such as are described herein. Tissue capture chambers 510 can comprise one or more materials selected from the group consisting of: a plastic; a liquid crystal polymer; a metal; stainless steel; a thermally conductive material; and combinations of these. Tissue capture chambers 510 can comprise a durometer of less than 63 D, such as less than 50 D, such as approximately 40 D. Each tissue capture chamber 510 can be sized and arranged to capture tissue when a vacuum is applied to tissue capture chamber 510. Each tissue capture chamber 510 can be attached (e.g. fixedly attached) to expandable element 530 via an adhesive with a glass transition temperature (Tg) of at least −60° C. and/or no more than 200° C., such as a Tg of at least 60° C. and/or no more than 90° C., such as a Tg of approximately 77° C. Alternatively or additionally, one or more tissue capture chambers 510 can be attached to expandable element 530 via visco elastic tape and/or thermal welding. Each tissue capture chamber 510 can be attached (e.g. fixedly attached) to expandable element 530 via an adhesive configured to support an elongation (e.g. without failure) of at least 1% and/or no more than 500%, such as an elongation of at least 100% and/or no more than 400%, such as an elongation of approximately 300%. Each tissue capture chamber 510 can comprise an outer diameter of at least 0.1 mm and/or no more than 10 mm, such as a diameter of at least 1 mm and/or no more than 5 mm, such as at diameter of at least 2.28 mm and/or no more than 2.30 mm, such as a diameter of approximately 2.29 mm. Each tissue capture chamber can comprise a length of at least 2.5 mm and/or no more than 500 mm, such as a length of at least 10 mm and/or no more than 50 mm, such as a length of at least 17.25 mm and/or no more than 17.75 mm, such as a length of approximately 17.5 mm. Each tissue capture chamber 510 comprises an opening 512. Each opening 512 can comprise a length of at least 0.25 mm, or at least 0.5 mm, or at least 1 mm, and/or no more than 20 mm, such as a length of at least 2 mm and/or no more than 10 mm, such as a length of at least 3.45 mm and/or no more than 3.65 mm, such as a length of approximately 3.55 mm. Each opening 512 can comprise a width of at least 0.1 mm and/or no more than 10 mm, such as a width of at least 0.5 mm and/or no more than 4 mm, such as a width of at least 1.48 mm and/or no more than 1.68 mm, such as a width of approximately 1.58 mm. Each opening 512 can comprise a depth of at least 0.1 mm and/or no more than 10 mm, such as a depth of at least 1 mm and/or no more than 4 mm, such as a depth of at least 1.9 mm and/or no more than 2.1 mm, such as a depth of approximately 2.0 mm. Each opening 512 can be defined by walls that extend from the outer surface of port 510.

Figure 1A:
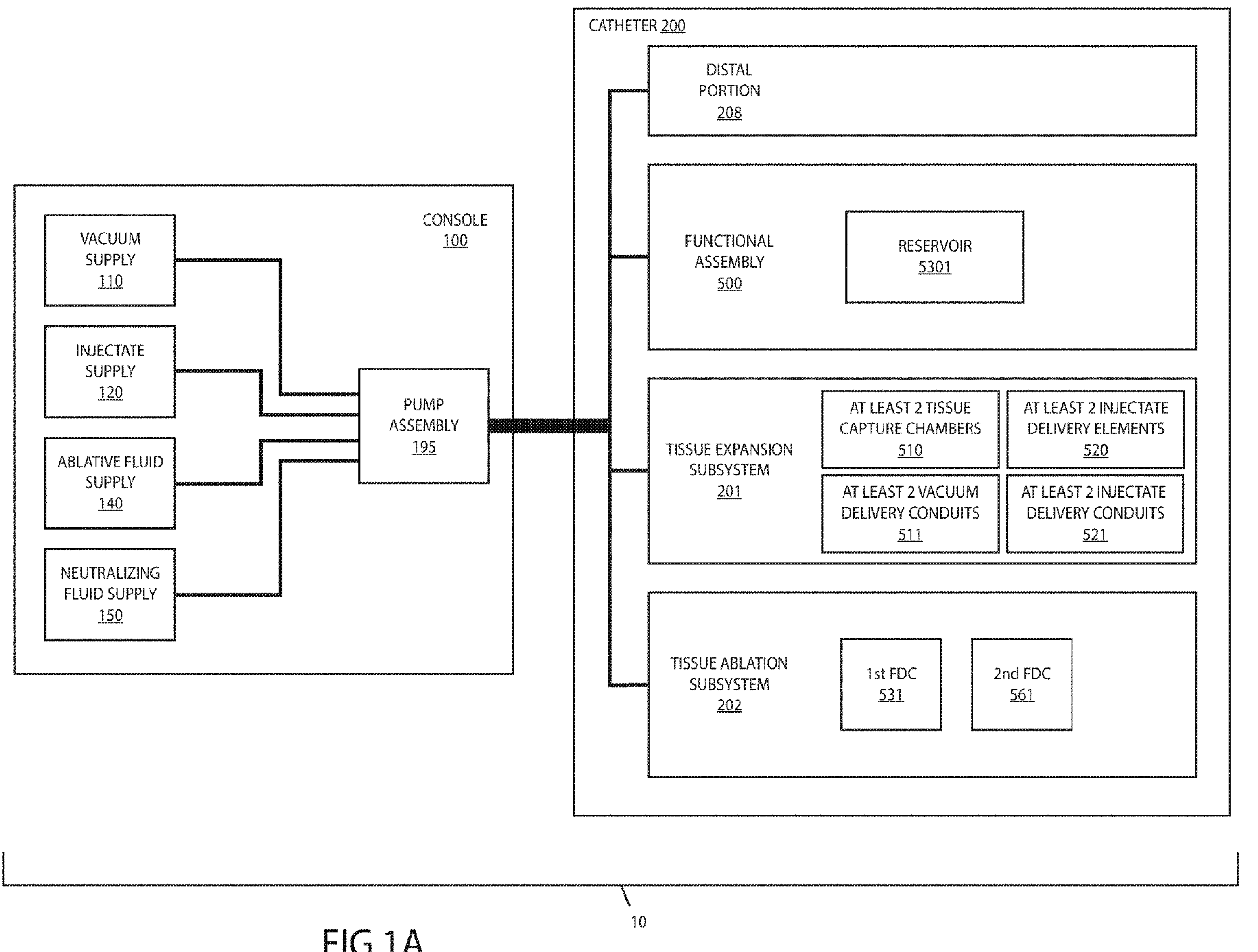
FIG. 1A illustrates a schematic view of a system for performing a medical procedure in the intestine of a patient, consistent with the present inventive concepts.

Referring now to FIG. 1A, a schematic view of a system for performing a medical procedure in the intestine of a patient is illustrated, consistent with the present inventive concepts. System 10 comprises console 100 and catheter 200. Console 100, catheter 200, and/or other components of system 10 of FIG. 1A can be of similar construction and arrangement to those described hereabove in reference to FIG. 1. Console 100 of FIG. 1A comprises at least vacuum supply 110, injectate supply 120, ablative fluid supply 140, and neutralizing fluid supply 150, each of which can be included within a single housing or multiple housings of console 100. Console 100 can include other fluid supplies and assemblies as described herein. Console 100 is fluidly and otherwise operatively attached to catheter 200, such as via an umbilical or other conduit, not shown but such as umbilical 600 described herein. Console 100 comprises one or more pumps, pumping assembly 195, which propels fluids between console 100 and catheter 200, also as described herein.

Catheter 200 comprises a distal portion 208 and a functional assembly 500 which can be positioned on distal portion 208. Functional assembly 500 comprises one or more balloons or other expandable reservoirs, such as reservoir 5301 shown. Console 100 can be configured to transport fluids into and out of reservoir 5301, such as to expand and contract, respectively, reservoir 5301, as described herein.

Catheter 200 further comprises a tissue expansion subsystem 201 configured to expand sub-surface tissue, such as submucosal tissue of the GI tract. Tissue expansion subsystem 201 can comprise conduits within catheter 200 which transport tissue expansion fluids to functional assembly 500 and provide a vacuum to functional assembly 500, each as described herein. Tissue expansion subsystem 201 can comprise at least two tissue capture chambers 510 configured to capture tissue when vacuum is applied via at least two vacuum delivery conduits 511 (e.g. vacuum provided by vacuum supply 110 of console 100). Tissue expansion subsystem 201 can comprise at least two injectate delivery elements 520 (e.g. needles or fluid jets) which can receive the tissue expansion fluid (e.g. injectate 125 provided by injectate supply 120 of console 100) via at least two injectate delivery conduits 521. Injectate delivery elements 520 can be configured to deliver the tissue expansion fluid to tissue captured by tissue capture chambers 510. One or more injectate delivery elements 520 can each comprise a needle configured to penetrate tissue (e.g. via advancement of the needle into chamber 510 when tissue is captured within the chamber 510 via the applied vacuum), after which fluid can be delivered into the tissue. Alternatively or additionally, one or more injectate delivery elements 520 can each comprise a fluid jet configured to deliver fluid through a surface of and into tissue captured within chamber 510.

Catheter 200 further comprises tissue ablation subsystem 202 comprising conduits within catheter 200 which transport ablation fluids and neutralizing fluids to and from functional assembly 500. Tissue ablation subsystem 202 comprises a first conduit, conduit 531, configured to provide fluid to functional assembly 500 (e.g. to reservoir 5301) and a second conduit, conduit 561, configured to remove fluid from functional assembly 500 (e.g. from reservoir 5301). Conduit 531 can be configured to provide to functional assembly 500 ablative fluid (e.g. fluid at an ablative temperature that is provided by ablative fluid supply 140 of console 100), as well as neutralizing fluid (e.g. neutralizing fluid provided by neutralizing fluid supply 150 of console 100 for cooling or warming of tissue prior to and/or after heat ablation or cryogenic ablation, respectively). Conduit 561 can be configured to remove ablative fluid and neutralizing fluid from functional assembly 500. In some embodiments, console 100 is configured to recirculate ablative fluid within functional assembly 500 (e.g. within one or more reservoirs of functional assembly 500), and to also recirculate neutralizing fluid within functional assembly 500 (e.g. within similar or dissimilar reservoirs of functional assembly 500). In some embodiments, console 100 is configured to sequentially recirculate ablative fluid and neutralizing fluid in a single reservoir (e.g. reservoir 5301) of functional assembly 500, such as to heat ablate tissue and subsequently cool tissue, or to pre-cool tissue and subsequently ablate tissue. In some embodiments, console 100 is configured to sequentially recirculate ablative fluid and neutralizing fluid in functional assembly 500 to pre-cool tissue, then ablate tissue, and then cool tissue.

Figure 1B:
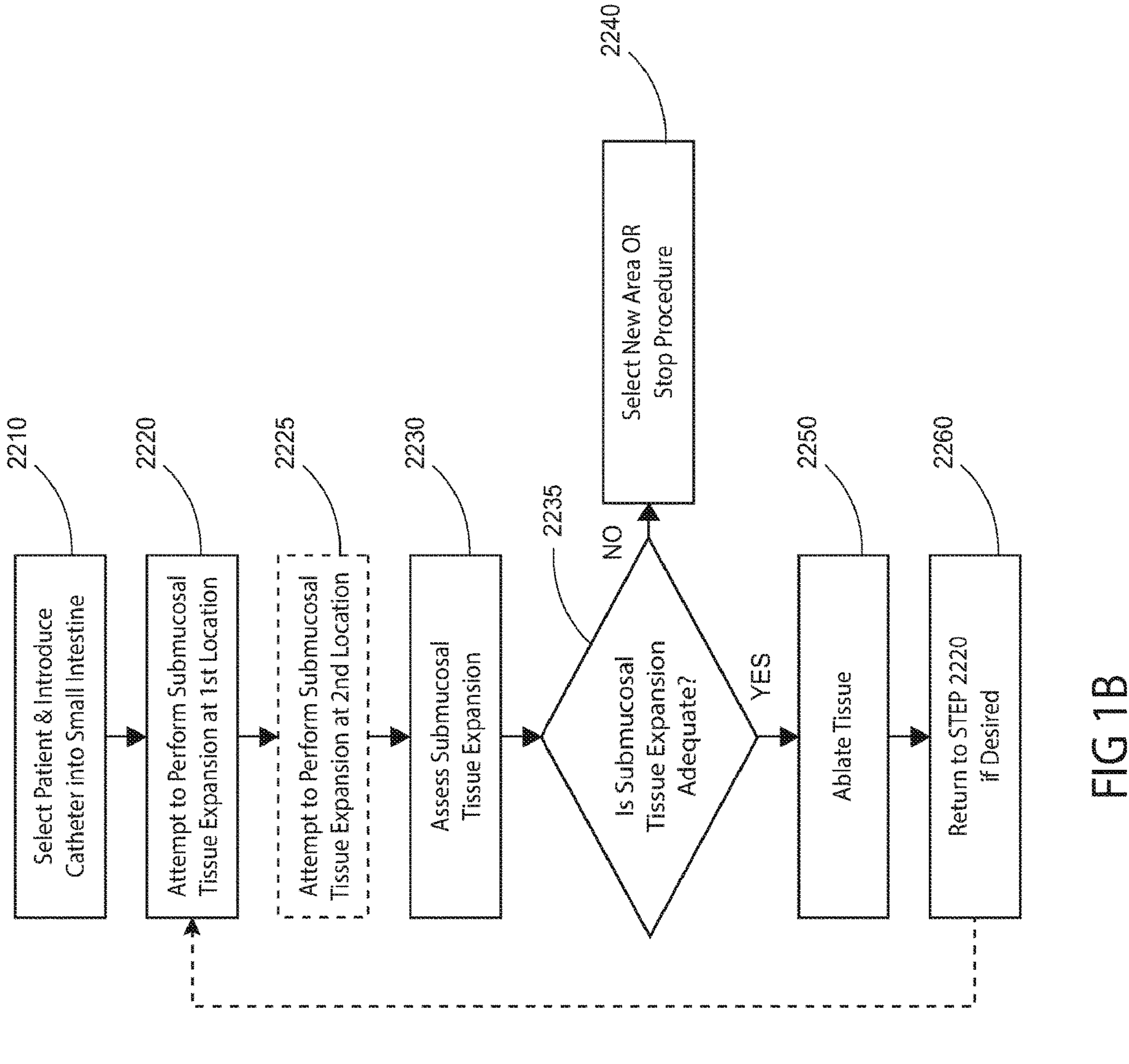
FIG. 1B illustrates a flow chart of a method of treating target tissue of a patient, consistent with the present inventive concepts.

Referring now to FIG. 1B, a flow chart of a method of treating target tissue of a patient is illustrated, consistent with the present inventive concepts. In some embodiments, the method 2200 of FIG. 1B is accomplished using system 10 of FIG. 1 or otherwise as described herein. In Step 2210, a patient is selected for treatment, such as a patient selected to treat and/or diagnose ("treat" herein) a patient disease or disorder selected from the group consisting of: Type 2 diabetes; Type 1 diabetes; "Double Diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome (PCOS); hypertriglyceridemia; hypercholesterolemia; psoriasis; GERD; coronary artery disease (e.g. as a secondary prevention); stroke; TIA; cognitive decline; dementia; Alzheimer's Disease; neuropathy; diabetic nephropathy; retinopathy; heart disease; diabetic heart disease; heart failure; diabetic heart failure; and combinations of these. In some embodiments, the patient is selected to treat two or more of the above diseases or disorders, such as a patient selected to treat two or more of diabetes, insulin resistance, NAFLD, NASH, and/or PCOS.

The patient selected can be taking one or more medicines to treat their diabetes. The patient selected can have an HbA1c level between 7.5% and 12.0%, between 7.5% and 10%, or between 7.5% and 9.0%. In some embodiments, the patient selected can have an HbA1c level between 6.0% and 12.0%. Patients with higher HbA1c levels and/or other higher disease burden can receive more aggressive treatments (e.g. more tissue treated and/or higher number of repeated treatments over time) as described herebelow in reference to Step 2250.

Patient selection can be based on the current level of one or more parameters representing one or more various biomarkers or other representative values of physiologic conditions (e.g. as compared to an average among diabetic and/or non-diabetic patients), such as a level of a parameter selected from the group consisting of: body mass index (BMI) level; waist circumference; HbA1c level; fasting glucose; insulin resistance; liver fibrosis; cholesterol or triglyceride level; duration of years exhibiting type 2 diabetes; fasting insulin, fasting C-peptide or C-Peptide stimulation in response to a meal; age; and combinations of these.

Prior to placing one or more devices into the patient (e.g. catheter 200), or at any time thereafter (e.g. during or after the procedure), one or more agents can be introduced into the patient. In some embodiments, one or more agents are introduced into the GI tract directly, such as agent 80 described hereabove in reference to FIG. 1. In some embodiments, agent 80 comprises L-menthol (i.e. oil of peppermint) or other agent configured to provide an anti-peristalsis effect. In these embodiments, a few drops of agent 80 can be placed in an irrigation or other lumen of an inserted device (e.g. endoscope 50). In some embodiments, approximately 8 mL of L-menthol is mixed with approximately 0.2 mL of Tween 80 (polysorbate 80) in approximately 500 mL of distilled water (i.e. to create an approximately 1.6% solution). Approximately 20 mL of this mixture can be sprayed through a working channel of endoscope 50, or more as required to dampen peristalsis. In some embodiments, the solution can vary between approximately 1.6% and 3.2%. Tween and/or sorbitan monostearate can be used as an emulsifier.

One or more agents 80 can be delivered once endoscope 50 or any other agent delivery device of system 10 enters the duodenum. In some embodiments, agent 80 comprises one or more agents that are delivered intravenously, and can include glucagon and/or buscopan.

As described herein, in some embodiments, an endoscope is inserted into the patient (e.g. endoscope 50 of FIG. 1). In these embodiments, subsequently inserted devices can be placed through a working channel of endoscope 50 and/or alongside endoscope 50. In some embodiments, endoscope 50 and an attachable sheath are both inserted into the patient, and subsequently inserted devices can be placed through a working channel of endoscope 50, through the attachable sheath, and/or alongside endoscope 50 and the attached sheath. Each device placed within the patient can be inserted over a guidewire. In some embodiments, an endoscope stiffening device is used, such as an endoscope stiffening system provided by Zutron Medical of Lenexa, Kansas, USA.

In some embodiments, non-target tissue is identified. Non-target tissue can be identified with a visualization device, such as endoscope 50 and/or imaging device 70 described herein. The non-target tissue can comprise the ampulla of Vater, the pancreas, and/or other tissue to which treatment (e.g. ablation) may adversely affect the patient. Marking of the non-target tissue (or tissue proximate the non-target tissue) can be performed, such as with a tattoo, ink or other visualizable substance, such as a visual agent or clip placed in and/or on the mucosa and/or submucosa in or proximate the ampulla of Vater. In some embodiments, one or more markers similar to marker 90 described hereabove in reference to FIG. 1 are deployed in the patient to provide a reference location relative to non-target tissue. Tissue expansion and/or tissue treatment performed in subsequent steps can avoid treating (e.g. avoiding delivering ablative energy to) the non-target tissue identified and potentially marked (e.g. with one or more markers 90).

Next in Step 2210, a treatment catheter, such as catheter 200 of FIG. 1, is inserted through the patient's mouth and advanced through the stomach and into the small intestine. Step 2210 can include selecting a particular model of catheter 200, such as a particular size (e.g. treatment element length and/or diameter) or other configuration of catheter 200. Catheter 200 can be inserted over guidewire 60, such as are described hereabove in reference to FIG. 1. Guidewire 60 can be advanced such that its distal end is in the jejunum or more distal location. During advancement of catheter 200, guidewire 60 can be held taut in order to prevent catheter 200 from forming a loop in the stomach. As described herein, catheter 200 can be inserted through a working channel of endoscope 50 and/or alongside endoscope 50.

Catheter 200 is advanced (e.g. over guidewire 60) such that functional assembly 500 is positioned in the duodenum (or another GI location). One or more tissue capture chambers 510 (e.g. three tissue capture chambers 510 positioned on expandable element 530 of functional assembly 500) can be positioned at a first location in the intestine. The first location can be a most-proximal target location to be treated, such as a location in the duodenum at least 0.5 cm or at least 1 cm, but not more than 5 cm or 10 cm from the ampulla of Vater. In some embodiments, tissue capture chambers 510 are positioned based on the location of a previously placed marker, such as marker 90 described herein. Prior to and/or during insertion of catheter 200, a stiffening wire can be inserted within catheter 200. Endoscope 50 can be positioned adjacent catheter 200, such that the distal ends of each are positioned beyond the ampulla of Vater (e.g. beyond marker 90).

In Step 2220, submucosal tissue expansion is performed, or at least attempted, at the first location (e.g. a first axial segment of the duodenum). Saline and/or other fluid or material (injectate 125) is injected into submucosal tissue. In some embodiments, injectate 125 is delivered (e.g. simultaneously injected) by multiple injectate delivery elements 520 of functional assembly 500, each element 520 positioned in a corresponding tissue capture chamber 510 (e.g. three chambers 510 spaced approximately 120° apart along a circumference). Each injection (by a single injectate delivery element 520) can comprise at least 1 mL, such as at least 2 mL, at least 5 mL or at least 8 mL per each injectate delivery element 520 (e.g. when the cumulative amount of fluid delivered by the multiple injectate delivery element 520 comprises at least 3 mL, such as at least 6 mL, at least 15 mL, or at least 24 mL). Each injection can comprise no more than 20 mL, such as no more than 15 mL, or when each injection comprises approximately 10 mL (e.g. when the cumulative amount of fluid delivered by the multiple injectate delivery element 520 comprises no more than 60 mL, such as no more than 45 mL, or when the cumulative amount comprises approximately 30 mL). In some embodiments, each injection comprises at least 4 mL, at least 6 mL, or at least 8 mL. In some embodiments, the volume of injectate delivered (e.g. via three circumferentially positioned injectate delivery elements 520) can be configured to achieve an expansion of the submucosal layer to a thickness of at least 250 m, or approximately 400 m, in the area surrounding the volume of mucosal tissue to be ablated. Console 100 can be configured to deliver injectate 125 at a flow rate of at least 1 mL/min, or at least 10 mL/min, such as a flow rate of 50 mL/min, or 100 mL/min. In some embodiments, console 100 is configured to deliver the full volume of injectate for a single injectate delivery element 520 at a single site within a time period of no more than 2 minutes, no more than 1 minute, or no more than 30 seconds. In some embodiments, injectate 125 is injected into tissue in a closed loop fashion, such as until a pressure threshold is reached (e.g. pressure within a delivery element), until the pressure within a balloon or other functional element placed proximate the injection site increases above a threshold, and/or until the inner diameter of the duodenum is reduced to a certain size or by a percentage of its pre-injection size.

Volumes injected by the multiple injectate delivery elements 520 can be selected to achieve near full circumferential expansion of submucosal tissue (e.g. without gaps, full 360° expansion). Each submucosal tissue expansion step is configured to create a safety margin of expanded submucosal tissue, as described herein, this expanded tissue volume (e.g. a partial or full circumferential tubular volume of the intestine) defining an "expanded tissue periphery". In some embodiments, functional assembly 500 is constructed and arranged (e.g. the ablative portion is sized) such that a submucosal tissue expansion performed at a single axial location of the small intestine (e.g. via delivery of injectate 125 via two, three or more injectate delivery elements 520, simultaneously or sequentially at the single axial location) creates an expanded tissue periphery that is sufficiently sized to surround an "ablation periphery" that is created during ablation via functional assembly 500 (as described herebelow in reference to Step 2250). This sufficiently sized expanded tissue periphery avoids transmission of significant energy beyond the submucosal layer (e.g. avoids transmission of energy at a level sufficient to ablate the deeper, muscular layers of the GI tract). For example, in cases of full circumferential submucosal tissue expansion, if the axial length of the expanded submucosal tissue achieved by injectate 125 delivery in Step 2220 is greater than the axial length of the tissue to be ablated, the submucosal tissue expanded is sufficient to provide a safety margin for the ablation (e.g. when during ablation functional assembly 500 is relatively centered within the expanded length of tissue).

In some embodiments, the expanded tissue periphery created in a single submucosal tissue expansion step is not sufficiently sized to support the ablation periphery created by functional assembly 500, and an optional Step 2225 is performed (e.g. one or more times), comprising additional submucosal tissue expansion. For example, a second submucosal tissue expansion can be performed at a neighboring (e.g. relatively adjacent and more distal) axial segment of the duodenum, such as by translating (e.g. advancing) catheter 200 to reposition functional assembly 500. Functional assembly 500 can be at least partially collapsed (e.g. ablation fluid 145, neutralizing fluid 155, and/or other fluid is removed from functional assembly 500) prior to translation. Translations of catheter 200 (advancements and/or retractions of functional assembly 500 or other portion of catheter 200) can be performed under visualized guidance, such as when functional elements **499*a*, 499*b* and/or 599 described herein comprise a radiopaque band or other visualization marker that can be visualized by imaging device 70 (e.g. a fluoroscope). Alternatively or additionally, rotations of catheter 200 (e.g. rotations of functional assembly 500 or other portion of catheter 200) can be performed under similar visualized guidance. In Step 2225, catheter 200 can be translated (e.g. advanced) a pre-determined distance (e.g. a distance of at least 0.3 cm, or at least 0.6 cm), after which delivery of injectate 125 can begin. Delivery of injectate 125 via the injectate delivery elements 520, as described hereabove in reference to Step 2220, creates a second (e.g. contiguous) volume of expanded submucosal tissue that in combination with the first expanded volume of submucosal tissue defines a larger expanded tissue periphery than that which is created in a single tissue expansion step. This larger expanded tissue periphery can support larger ablation peripheries (e.g. longer full circumferential lengths of tissue to be ablated), such as may be required by functional assembly 500 in a single ablation. For example, in cases of full circumferential submucosal tissue expansion, if the axial length of the expanded submucosal tissue achieved by injectate 125 delivery in the combined deliveries of Step 2220 and Step 2225** is greater than the axial length of the tissue to be ablated, the submucosal tissue expanded is sufficient to provide a safety margin for the ablation.

Figure 1C:
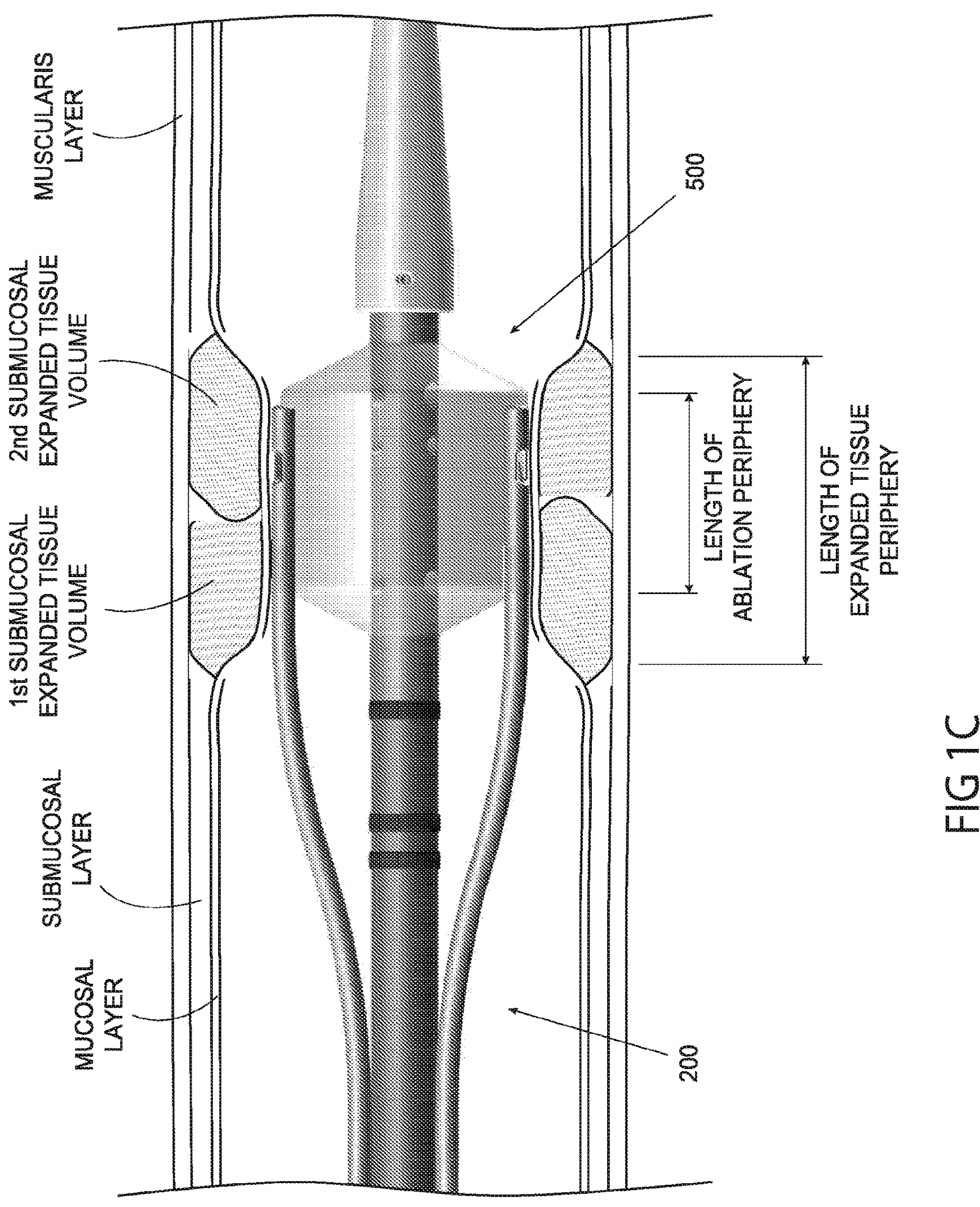
FIG. 1C illustrates a sectional anatomical view of a treatment device inserted into a gastrointestinal lumen, consistent with the present inventive concepts.

Referring additionally to FIG. 1C, a representative expanded periphery and ablation periphery of two full circumferential expansions followed by a single full circumferential ablation, each performed by catheter 200 via console 100 as described herein, are illustrated. A first and second circumferential submucosal tissue expansion combine to form an expanded tissue periphery with a length as shown. Functional assembly 500 can deliver energy to an ablation periphery that is positioned within the expanded tissue periphery.

Optional Step 2225 can be performed two or more times, resulting in three or more injections of fluid into tissue (e.g. submucosal tissue), with or without an intervening ablation performed via Step 2250. Sequential injections of injectate 125 can be performed at an axial separation distance of between 1 cm and 2 cm apart from a previous injection (e.g. 1 cm to 2 cm distally in the duodenum, jejunum, or other GI location). In some embodiments, multiple injections are positioned at least 0.5 cm apart along the axis of the small intestine, such as between 1.0 cm and 5.0 cm apart, such as approximately 1.0 cm, 2.0 cm, 3.0 cm, 4.0 cm and/or 5.0 cm apart from one another along the axis of the small intestine. In some embodiments, axial separation of injection sites (i.e. translation distance of catheter 200 between injections) can approximate half the length of expandable element 530 onto which injectate delivery elements 520 are mounted, such as half the length of expandable element 530 of FIG. 1. In some embodiments, a series of 5-15 sets (e.g. 8-12 sets) of injections (e.g. each set comprising injections from 2, 3 or more injectate delivery elements 520) can be performed (with or without an intervening ablation step) by delivering injectate 125 (e.g. a fluid containing a visualizable dye) to the tissue to be expanded and subsequently translating catheter 200 to a new axial location (e.g. after proper expansion of tissue is confirmed visually as described herebelow in Steps 2230 and 2235, or otherwise). Each advancement and/or retraction of catheter 200 can be made in unison with advancement and/or retraction of an endoscope positioned alongside catheter 200.

As described herein, tissue expansion can begin at a location proximate but distal to the ampulla of Vater, such as at a location at least 1 cm distal to but not more than 5 cm or 10 cm from the ampulla of Vater. A series of relatively contiguous, full circumferential submucosal tissue expansions can be performed (e.g. moving distally), for example to a distal location up to the Ligament of Treitz. In alternate embodiments, multiple full circumferential tissue expansions are performed by moving catheter 200 from distal to proximal locations, or in a discontinuous (back and forth) manner.

Volumes of injections and/or axial separation of injection sites can be chosen to avoid axial gaps between neighboring expanded volumes of tissue (e.g. when an ablation step is to be performed proximate one or both expanded volumes of tissue). After injections, gaps identified circumferentially and/or axially (e.g. via endoscope camera, fluoroscope or ultrasound imaging device), can be filled in as deemed necessary via additional injection (e.g. with or without rotation and/or translation of catheter 200).

In some embodiments, console 100 is configured to reduce the amount of fluid (e.g. liquid such as water or gas such as air or carbon dioxide) in expandable element 530 supporting injectate delivery elements 520 as the injectate 125 is delivered into tissue, such as to prevent excessive force being applied to tissue proximate the expanding tissue (i.e. due to the decreasing lumen of the intestine proximate the expanding tissue in contact with expandable element 530).

Multiple injections (e.g. two, three or more injections from two, three or more equally separated injectate delivery elements 520) can be performed simultaneously or sequentially in a single axial segment of the intestine (e.g. without moving functional assembly 500). A vacuum can be applied (e.g. automatically or otherwise via system 10, such as via a working channel of endoscope 50 and/or via ports 470P or 470D of catheter 200) to the intestinal lumen (e.g. desufflation) prior to delivery of injectate 125, such as to draw tissue toward each injectate delivery element 520 (e.g. into the associated chambers 510). After injectate 125 delivery, the vacuum can be removed and an ablation performed (e.g. in Step 2250 below without additional translation or other movement of functional assembly 500), or catheter 200 can be advanced (or retracted) for a subsequent (additional) tissue expansion.

In Step 2230, an assessment of submucosal tissue expansion is performed (e.g. manually by an operator and/or automatically by system 10). Step 2230 can be performed after Step 2225, as shown in FIG. 1B (e.g. if Step 2225 is performed), and/or directly after Step 2220 (e.g. when a single tissue expansion is sufficient for the subsequent ablation or simply when an assessment is desired directly after a tissue expansion). In some embodiments, assessment of submucosal tissue expansion is performed via a camera view provided by endoscope 50 (e.g. an endoscope with a camera positioned to view the submucosal tissue expansion). Alternatively or additionally, submucosal tissue expansion can be performed using a visualization device of system 10, such as when imaging device 70 described hereabove in reference to FIG. 1 provides one or more images used to perform the assessment. Injectate 125 delivered in Steps 2220 and/or 2225 can include an agent that is directly visualizable by an operator and/or an agent whose location (e.g. a volume of tissue that has been expanded by injectate 125) can be (at least partially) assessed by system 10 (e.g. via an image processing algorithm of console 100 or other component of system 10). For example, injectate 125 can comprise a material selected from the group consisting of: a visible material (such as India Ink, Indigo Carmine, and the like) visualized by an endoscope 50 camera, catheter 200 camera (e.g. when functional element 599 comprises a camera), or other camera; a radiopaque material visualizable by an imaging device 70 comprising a fluoroscope or other X-ray imaging device; an ultrasonically reflectable material visualizable by an imaging device 70 comprising an ultrasound imaging device; any visualizable material; and combinations of one or more of these. Visualization of the expanded tissue can be used to determine (e.g. automatically determine by algorithm 11) that a proper volume of injectate has been delivered as well as sufficient tissue expansion has been achieved, such as to ensure sufficient thickness, elimination of gaps, sufficient axial length, and/or sufficient circumferentially (e.g. full or near-full circumferential nature) of tissue expansion has occurred. The pressure of expandable element 530 or the volume of fluid within expandable element 530 can also be monitored to determine if a proper volume of injectate has been delivered to achieve adequate tissue expansion. In particular, the expanded tissue can be analyzed to identify areas of relatively poor expansion which may indicate regions of adherent submucosal tissue (such as scarred and/or fibrotic submucosal tissue not amenable to tissue expansion).

As described above, in some embodiments, assessment of submucosal tissue expansion performed in Step 2230 is performed (at least) using a camera of endoscope 50. In these embodiments, prior to and/or during the assessment of submucosal tissue expansion performed in Step 2230, functional assembly 500 can be at least partially collapsed (e.g. inflation fluid 135, and/or other fluid is removed from functional assembly 500), to provide an increased view of the expanded tissue. Alternatively or additionally, functional assembly 500 is at least partially collapsed to allow advancement of endoscope 50 toward and potentially into the axial segment of intestinal tissue to which the submucosal tissue has been expanded, to provide a closer view of the expanded tissue.

In Step 2235, adequacy of submucosal tissue expansion is determined (e.g. a qualitative assessment performed by a clinician and/or a quantitative assessment performed automatically and/or semi-automatically using system 10). If submucosal tissue expansion is determined to be inadequate, Step 2240 is performed, in which a new (alternative) area for tissue expansion and subsequent ablation is selected, or the procedure is terminated (e.g. after limited or no ablations have been performed). In some embodiments, the method 2200 of FIG. 1B is included in a medical procedure that is performed on a patient after (e.g. at least 24 hours after) a similar procedure has been performed on that same patient (e.g. a similar ablation procedure in the duodenum or other location of the patient's small intestine or GI tract). The assessment of submucosal expansion performed in Step 2230 can be an important diagnostic test that can confirm that it is safe to perform a repeated, similar procedure (e.g. the procedure of the present inventive concepts). Alternatively, the assessment may enable the identification of patients who may have: an active infection in their small intestine; a history of infection (such as tuberculosis) and/or malignancy that can cause a GI segment injury (e.g. a condition that may make submucosal expansion challenging or even impossible); and combinations of these, such as patients to which no or limited ablations should be performed. For example, there may be significant fibrosis and/or significant scar present at a target location (from a previous procedure or otherwise), which could prevent proper submucosal tissue expansion. In these instances, ablation should not be performed, at least not at that location of the intestine.

If the submucosal tissue expansion is determined to be adequate, Step 2250 is performed in which target tissue is treated (e.g. ablated) by functional assembly 500 of catheter 200. The target tissue can comprise one or more portions of the mucosal layer of the duodenum, jejunum, and/or other GI location proximate (e.g. on top of) the submucosal tissue that has been previously expanded (e.g. in one or more expansion steps 2220 and/or 2225). Treated tissue can further comprise at least an inner layer of neighboring submucosal tissue (e.g. a partial depth of the submucosal tissue layer previously expanded). In some embodiments, the ablation of Step 2250 is performed without repositioning (e.g. without translating) functional assembly 500, such as without repositioning after Step 2220 or without repositioning after Step 2225 (if the optional step is performed), such as to ensure that ablation is performed over an area of expanded submucosal tissue (e.g. over a sufficiently sized expanded tissue periphery as defined herein) that provides a safety margin to avoid adversely affecting tissue layers beyond (deeper than) the submucosal layer. One or more circumferential ablations, partial circumferential ablations, and/or other treatments can be performed along a length of the GI tract (e.g. along one or more axial segments of the GI tract), such as along a length of the duodenum at least 1 cm distal to the ampulla of Vater, such as at a location at least 1 cm distal to but within 3 cm, 5 cm or 10 cm of the ampulla of Vater. In some embodiments, all ablations are performed at least 2 cm or at least 3 cm distal to the ampulla of Vater (e.g. tissue within 1 cm, 2 cm or 3 cm of the ampulla of Vater is not ablated). In some embodiments, tissue treatments are only performed at locations that have had submucosal tissue expansion performed and/or confirmed (e.g. visually as described hereabove in reference to Step 2230 and 2235).

In some embodiments, step 2250 is performed immediately following step 2220 or step 2225 (e.g. without performing an assessment of the submucosal tissue expansion). Step 2250 can be performed without repositioning functional assembly 500 between the expansion and step 2250. In some embodiments, system 10 is configured to monitor (e.g. via one or more functional elements of system 10 as described herein) one or more parameters of the submucosal tissue expansion (e.g. during steps 2220 and/or 2225), for example the volume of expansion fluid delivered. If the parameters are within acceptable values, step 2250 can be performed without performing steps 2230 and/or 2235.

In some embodiments, a thermal ablation is provided by sufficiently hot or sufficiently cold fluid introduced into expandable element 530 to ablate tissue. Alternatively or additionally, different forms of energy delivery or other tissue treatments can be performed (e.g. electromagnetic energy, light energy, mechanical energy and/or chemical energy).

Catheter 200 and console 100 can be configured to treat a series of axial segments of GI tract tissue comprising lengths between 1 cm and 5 cm each, such as approximately 2 cm in length each. Catheter 200 and console 100 can be configured to treat a cumulative axial length of GI tract tissue (e.g. an axial length of duodenal mucosal tissue) of less than or equal to 3 cm, 6 cm, 9 cm, 15 cm, or 20 cm. Catheter 200 and console 100 can be configured to treat more than 3 cm of axial length of duodenal mucosa, such as more than 3.4 cm, more than 6 cm, more than 7 cm, more than 8 cm or more than 9 cm (e.g. approximately 9.3 cm). In some embodiments, at least 10%, 15%, 25%, 30% and/or 50% of the duodenal mucosa distal to the ampulla of Vater is treated. The axial length and/or overall volume of tissue treated can correspond to a patient parameter, such as the longevity of the disease or other disease parameter as described herein (e.g. higher disease burden correlating to larger volumes of tissue treated).

In some embodiments, at least 3 axial segments of duodenal mucosal tissue are treated (e.g. sequentially ablated, such as a sequential treatment including at least one submucosal tissue expansion step performed before each ablation), such as with a functional assembly 500 configured to deliver energy to a delivery zone with a length between 0.5 cm and 4.0 cm (e.g. tissue contacting length of expandable element 530 filled with ablative fluid), such as a delivery zone length (e.g. tissue contacting length) between 0.5 cm and 4.0 cm, between 1.5 cm and 3.3 cm, or approximately 2 cm in length. In some embodiments, at least 4 axial segments of duodenal mucosal tissue are treated, such as when at least 6 axial segments of duodenal mucosal tissue are treated. In these embodiments, functional assembly 500 can be configured to deliver energy to a delivery zone with a length between 0.7 cm and 2.0 cm (e.g. tissue contacting length of expandable element 530 filled with ablative fluid). In some embodiments, functional assembly 500 comprises ablative fluid delivered into expandable element 530 (e.g. ablative fluid 145 provided by console 100). Multiple tissue treatments are performed by repositioning functional assembly 500, which can further include contracting expandable element 530 to reposition functional assembly 500. Contact between the target tissue and functional assembly 500 can be accomplished using desufflation techniques to bring the tissue toward expandable element 530 and/or via expansion of expandable element 530. Tissue treatment is performed, such as by filling expandable element 530 with ablative temperature fluid and/or delivering any form of energy to the target tissue. In embodiments where catheter 200 is delivered over a guidewire, the guidewire can be retracted (e.g. at least retracted to a location proximal to the treatment element) prior to any tissue treatments (e.g. prior to any energy deliveries).

Multiple treatments can be performed by advancing or retracting functional assembly 500 and/or catheter 200. In some embodiments, functional assembly 500 is positioned at a distal location and a series of tissue treatments are performed, such as at least 3 tissue treatments performed in which catheter 200 is retracted approximately the length of the tissue contacting portion of functional assembly 500 such as to treat relatively contiguous, non-overlapping, full circumferential axial segments of the duodenum (e.g. where at least one submucosal tissue expansion is performed prior to each ablation or other treatment). Prior to each treatment, an assessment of adequate submucosal tissue expansion can be performed, as described herein. Also prior to each tissue treatment, confirmation of being away from (e.g. distal to) any non-target tissue marked and/or otherwise identified can be performed (e.g. by visualizing a previously placed marker 90). In some embodiments, a marker 90 is placed to avoid any damage to the ampulla of Vater. In some embodiments, after three axial segments of duodenal mucosa are treated (e.g. treated distally to proximally), an assessment of the linear distance between the most-proximal treatment segment and the ampulla of Vater is performed (e.g. one or more components of system 10 is used to determine the distance). If sufficient length is determined (e.g. the determined distance is above a threshold), additional (more proximal) axial tissue segments can be treated. During translation of catheter 200 over a guidewire, undesired movement of the guidewire is prevented or otherwise reduced by the operator.

In some embodiments, the system of the present inventive concepts (e.g. system 10 of FIG. 1) is configured to allow only one ablation per (pre-determined) time period, such as to prevent two ablations within the time period such as to prevent repetitive ablation in the same or at least similar (e.g. overlapping) portions of the GI tract (e.g. rapid treatment of similar treatment zones).

In some embodiments, the tissue treatment of Step 2250 should be completed within approximately 120 minutes or within approximately 60 minutes of the initiation of tissue expansion performed in Step 2220 and/or step 2225, such as within approximately 45 minutes, 30 minutes and/or 20 minutes. Performance of tissue treatment within this time window prevents an unacceptable amount of injectate 125 from dissipating beyond the expanded submucosal tissue space (e.g. prevents an insufficient amount of submucosal tissue expansion being present during the tissue treatment). In some embodiments, system 10 is configured to prevent a tissue treatment (e.g. ablation) until an adequate submucosal expansion step has been performed and/or confirmed, such as is described in Step 2230. After one or more axial segments of duodenum or other GI segment is ablated in Step 2250, a determination is made in Step 2260 regarding additional axial segments to be treated. In some embodiments, a single axial segment is ablated in Step 2250, after which additional submucosal tissue is expanded (e.g. in one or more of Steps 2220 and/or 2225) and an additional ablation is performed proximate the additionally expanded submucosal tissue. In some embodiments, two axial segments of submucosal tissue are expanded for each single axial segment of mucosal tissue ablated. In some embodiments, a first ablation is performed proximate an area of two submucosal expansions (e.g. directly after the two submucosal expansions are performed), and subsequent ablations are performed after (e.g. directly after) two or less (e.g. one) submucosal expansions are performed (e.g. expansions performed in the area of the subsequent ablations).

The cumulative amount of target tissue treated and/or the number of treatments performed can correlate to (e.g. be proportional to) one or more patient conditions (e.g. more severe correlates to more tissue treated and/or more treatments performed over time). This increased treatment can comprise an increased axial length of tissue treated (e.g. an increased cumulative axial length of duodenum ablated), an increased volume of tissue treated (e.g. an increased volume of duodenal mucosa treated via an increased mucosal surface area receiving ablation energy from functional assembly 500), a deeper depth of treatment, and/or a larger number of treatments performed over time in order to achieve a sustained treatment response. In some embodiments, the tissue treatment is modified to avoid creation of a duodenal stenosis or stricture, such as to limit one or more of: amount of energy delivered; peak energy delivered; duration of energy delivered; length of tissue treated; depth of tissue treated; and combinations of these.

Figures 2A, 2B:
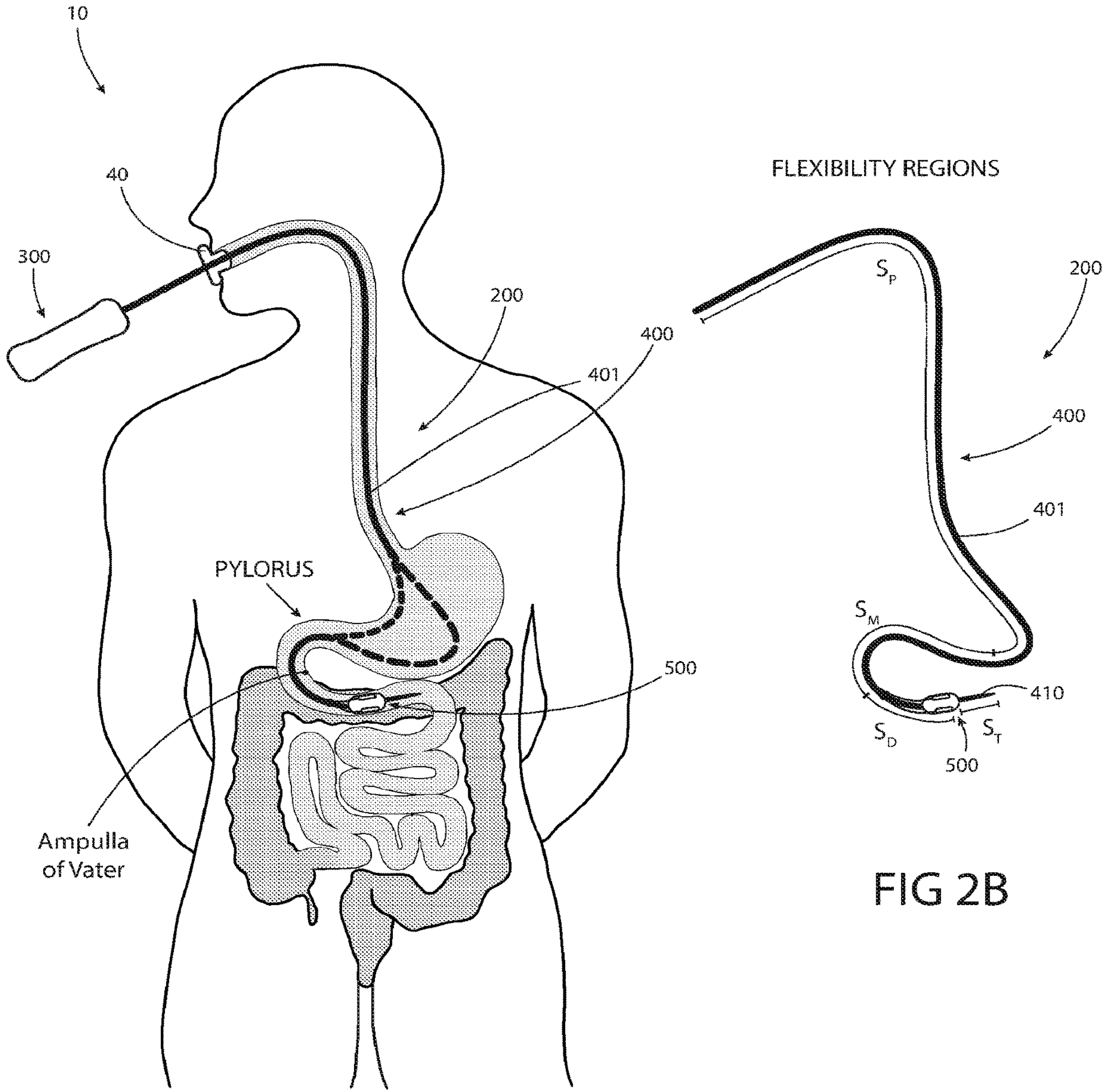
FIGS. 2A and 2B illustrate schematic views of a catheter inserted into a patient and that catheter shown in an anatomical shape, consistent with the present inventive concepts.

Referring now to FIGS. 2A and 2B, schematic views of a catheter inserted into a patient and that catheter shown in an anatomical shape (e.g. a shape the catheter assumes when inserted into a patient) are illustrated, respectively, consistent with the present inventive concepts. As described herein, catheter 200 is configured to be inserted into a patient's GI tract via the mouth. In FIG. 2A, catheter 200 is shown inserted through an introduction device 40, such as a bite block. Catheter 200 can be configured to track within the anatomy of the patient (e.g. follow a natural anatomic path, such as the GI tract) to reach one, two, or more locations to perform a treatment procedure (e.g. a mucosal or other tissue treatment procedure). In some embodiments, catheter 200 is configured to be advanced over a guidewire, such as when the distal portion of a guidewire has been positioned within the small intestine of the patient prior to the introduction of catheter 200 into the small intestine. Catheter 200 is shown inserted into the patient with functional assembly 500 positioned within the patient's duodenum, specifically with assembly 500 positioned distal to the pylorus and the ampulla of Vater. For example, catheter 200 can be advanced through the mouth of the patient, through the esophagus, and into the patient's stomach. Once in the stomach, catheter 200 can be further advanced, such that the distal end of catheter 200 tracks through the pylorus and enters the small intestine. Functional assembly 500 is shown advanced through the pylorus, into the duodenum, and positioned at a treatment location (e.g. in contact with target tissue) distal to the ampulla of Vater. Catheter 200 is shown in both a "long position" and a "short position", depicted with long and short dashes, respectively. The long position is achieved when a portion of shaft 401 is pressing against a wall of the stomach, following the curvature of the stomach from the end of the esophagus to the pylorus. The short position is achieved when catheter 200 follows a shorter path between the end of the esophagus and the pylorus. In FIG. 2B, catheter 200 is shown in the long position.

As described herein, catheter 200 can be advanced into the small intestine of a patient, where at least one (such as two) submucosal expansions can be performed prior to an ablative treatment. Catheter 200 can then be advanced, and a subsequent set of expansions and ablation can be performed. In some embodiments, an operator first places guidewire 60 into the small intestine of the patient following the long position illustrated (e.g. using endoscope 50, not shown). Catheter 200 is then advanced into the proximal end of the duodenum following guidewire 60 (along the long position illustrated). Endoscope 50 can then be positioned next to (e.g. parallel to) catheter 200, such that the proximal end of expandable element 530 is visible via endoscope 50. In some embodiments, at least the distal portion of endoscope 50 is positioned next to catheter 200 (e.g. in the small intestine of the patient), and at least a proximal portion of endoscope 50 is next to at least a proximal portion of catheter 200 (e.g. in the esophagus of the patient). Once both catheter 200 and endoscope 50 are positioned at least through the pylorus, catheter 200 and endoscope 50 can be advanced simultaneously into the duodenum, such that expandable element 530 is positioned distal to the ampulla of Vater. In some embodiments, catheter 200 and endoscope 50 are advanced simultaneously to reduce friction between the two devices and/or to limit the force required to advance either of the two devices individually. A set of expansions and an ablation can then be performed, with an approximately 1 cm advancement of both catheter 200 and endoscope 50 between each expansion. After each ablation, catheter 200 and endoscope 50 can be advanced such that expandable element 530 is distal to a previous ablation site using endoscopic visualization, such as to prevent ablating the same site twice.

Shaft assembly 400 of catheter 200 can comprise one, two, or more discrete, contiguous axial sections ("sections" herein), where each section can comprise a different hardness and/or stiffness ("stiffness" herein). Alternatively or additionally, shaft assembly 400 and/or a section of shaft assembly 400 can comprise a continuously variable stiffness. A stiffness profile for shaft assembly 400 can be selected to enhance the pushability, rotation, and/or trackability ("trackability" herein) of catheter 200 (e.g. the ease at which catheter 200 is advanced through and/or retracted within the anatomy of the patient). Stiffness of each section of shaft assembly 400 is determined by the properties (e.g. hardness) of the materials used to manufacture (e.g. extrude) the particular section of shaft 401, the geometry of shaft 401 of that section (e.g. geometry of lumens, wall thicknesses, and the like), as well as the properties of the components positioned within one or more lumens of that section of shaft 401.

Shaft 401 can comprise multiple sections, each with a different stiffness (e.g. a minimally varying stiffness along the length of the section), and/or it can include one or more sections with a varying (e.g. continuously varying) stiffness. In some embodiments, shaft assembly 400 of catheter 200 comprises three sections, sections $S_P$, $S_M$, and $S_D$, shown in FIG. 2B, each with a different stiffness. Catheter 200 can comprise a distal tip, tip 410, such as a tip with a tapered shape as shown. In some embodiments, shaft 401 terminates at the distal end of functional assembly 500, and tip 410 comprises a shaft that extends from the distal end of shaft 401. Alternatively or additionally, tip 410 can comprise the distal portion of shaft 401, such as a tapered portion of shaft 401 extending beyond the distal end of functional assembly 500. Section $S_P$ can comprise the proximal portion of shaft 401, extending distally from handle 300; section $S_M$ can comprise a middle section of shaft 401, adjacent and distal to section $S_P$; and section $S_D$ can comprise a distal section of shaft 401 adjacent and distal to section $S_M$ (e.g. the portion of shaft 401 immediately proximal to functional assembly 500), each as shown. In some embodiments, catheter 200 comprises a fourth section, section $S_T$, comprising at least the distal tip 410 of shaft 401, also as shown. Sections $S_P$, $S_M$, and $S_D$ can be similar and/or dissimilar to proximal portion 406, middle portion 407, and distal portion 408 of shaft assembly 400, respectively, described herein in reference to FIG. 1. For example, sections $S_P$, $S_M$, and/or $S_D$ can each comprise a discrete length of shaft assembly 400, each section spanning some or all of the length of one or more of portions 406, 407, and/or 408.

Each section $S_P$, $S_M$, $S_D$, and/or $S_T$ can comprise a stiffness similar or dissimilar from the stiffness of an adjacent section. In some embodiments, section $S_P$ comprises a first stiffness, section $S_M$ comprises a second stiffness, section $S_D$ comprises a third stiffness, and section $S_T$ comprises a fourth stiffness, where two, three, or four (all) of these sections comprise different stiffnesses. In some embodiments, the stiffness of section $S_P$ can comprise the highest stiffness, the stiffness of section $S_M$ can comprise the second highest stiffness, the stiffness of section $S_D$ can comprise the third highest stiffness, and/or the stiffness of section $S_T$ can comprise the lowest stiffness (e.g. each successive section of catheter 200 has a lower stiffness than the adjacent proximal section). In some embodiments, section $S_P$ of shaft 401 comprises a higher stiffness (e.g. higher relative to the other sections of catheter 200), such as a stiffness configured to aid in the trackability of catheter 200 (e.g. the ability to advance catheter 200 into the anatomy of the patient without kinking or other undesired deformation). Section $S_D$ of shaft 401 can comprise a relatively flexible section (e.g. lower stiffness than sections $S_P$ and/or $S_M$), such as a stiffness configured to enable a smaller bend radius than the more proximal sections, enhancing the trackability of catheter 200 (e.g. the trackability of the distal portion of catheter 200 through tortuous portions of the anatomy). Section $S_M$ can comprise a relatively medium stiffness (e.g. a stiffness at a level between that of sections $S_P$ and $S_D$), configured to maintain an adequate pushability of catheter 200 while being flexible enough to follow section $S_D$ through anatomical bends in the patient, such as the path through the stomach, pylorus, and into the duodenum.

In some embodiments, a stiffness change between two adjacent sections of shaft 401 occurs over a relatively short stiffness transition (e.g. an abrupt transition) or a relatively long transition of stiffness. For example, a short stiffness transition can comprise a distance of less than 2.5", less than 1.5", or less than 1", while a long stiffness transition can comprise a distance of at least 6", at least 12", or at least 18". Stiffness transitions between two adjacent sections of shaft 401 can be created during a manufacturing process of shaft 401. For example, a butt-welding of the two sections can include a reflow of the materials of the two sections (e.g. a reflow of two materials of different hardness). Alternatively or additionally, an extrusion process used to create at least the two sections of shaft 401 can be configured to controllably vary the stiffness of the manufactured extrusion (e.g. the resultant extrusion can include a material change at the transition that includes mixing of two or more materials). Long transitions in stiffness can be included to prevent or at least limit kinking of shaft 401 (e.g. to limit kinking in the transition regions of shaft 401).

In some embodiments, shaft 401 comprises an extrusion that gradually transitions from a first stiffness at the proximal end of shaft 401 to a second, lesser stiffness at the distal end of shaft 401 (e.g. via an extrusion process as described herein). In these embodiments, the stiffness transition can be uniform along the length of shaft 401. Alternatively, as described herein, the transition can be varied, such that the sections of shaft 401 maintain a near constant stiffness and the stiffness transitions gradually (e.g. over at least 2.5") between sections $S_P$, $S_M$, $S_D$, and/or $S_T$.

Section $S_P$ can comprise at least a first $S_P$ material, such as a material with a durometer of at least 63 D or 70 D, such as a material with a durometer of approximately 63 D, or 80 D. In some embodiments, section $S_P$ comprises this first $S_P$ material (e.g. polyether block amide) and one or more additives such as a lubricant, a plasticizer, and/or a radiopaque additive (e.g. barium sulfate at a 20% concentration), where the inclusion of these one or more additives can change (e.g. increase) the durometer of the section. Section $S_M$ can comprise at least a first $S_M$ material, such as a material with a durometer of approximately 55 D. Similar to section $S_P$, section $S_M$ can comprise this first $S_M$ material (e.g. polyether block amide) and one or more additives such as a lubricant, a plasticizer, and/or a radiopaque additive (e.g. barium sulfate at a 20% concentration), where the inclusion of these one or more additives can change (e.g. increase) the durometer of the section. Section $S_D$ can comprise at least a first $S_D$ material, such as a material with a durometer of approximately 40 D. Similar to sections $S_P$ and/or $S_M$, section $S_D$ can comprise this first $S_D$ material (e.g. polyether block amide) and one or more additives such as a lubricant, a plasticizer, and/or a radiopaque additive (e.g. barium sulfate at a 20% concentration), where the inclusion of these one or more additives can change (e.g. increase) the durometer of the section. In some embodiments, at least one section of shaft 401 comprises a mixture of at least 5% of a radiopaque material, such as at least 10%, such as at least 20%, such as at least 30%, such as at least 40%. Section $S_T$ can comprise at least a first $S_T$ material, such as a material with a durometer of approximately 35 D. Similar to sections $S_P$, $S_M$, and/or $S_D$, section $S_T$ can comprise this first $S_T$ material (e.g. polyether block amide) and one or more additives such as a lubricant, a plasticizer, and/or a radiopaque additive (e.g. barium sulfate at a 20% concentration), where the inclusion of these one or more additives can change (e.g. increase) the durometer of the section. Tip 410 can comprise a taper (e.g. a taper such that the distal portion of tip 410 comprises a smaller diameter than the proximal portion of tip 410). In some embodiments, the taper and/or other geometric feature (e.g. wall thickness variation) of tip 410 is configured such that the proximal portion of tip 410 comprises a stiffness greater than guidewire 60, and the distal portion of tip 410 comprises a stiffness less than guidewire 60 (e.g. guidewire 60 which can be slidingly positioned within catheter 200, exiting the distal portion of tip 410). In some embodiments, the proximal end of tip 410 comprises a stiffness approximately equal to the stiffness of the distal end of section $S_D$. In some embodiments, section $S_D$ and/or $S_T$ comprises at least one material (e.g. polyether block amide) with a durometer of less than 40 D, such as less than 30 D, such as less than 20 D, such as approximately 10 D.

Section $S_P$ can comprise a length long enough to reach the pylorus of the patient when catheter 200 is fully inserted into the patient. In some embodiments, the length of sections $S_P$, $S_M$, and/or $S_D$ are selected to enable catheter 200 to be advanced into the patient such that functional assembly 500 can be positioned at least 15" into the duodenum, such as at least 18" into the duodenum. In some embodiments, section $S_P$ comprises a length of at least 32", such as at least 49", such as no more than 72", such as approximately 57". Section $S_M$ can comprise a length of at least 10", such as approximately 17". Section $S_D$ can comprise a length of at least 2", such as approximately 5". In some embodiments, the transition between section $S_M$ and $S_D$ is co-located with manifold 700*d* (e.g. manifold 700*d* is positioned over the transition point between sections $S_M$ and $S_D$). In these embodiments, manifold 700*d* can be configured to provide a reinforcing support to shaft 401 at the transition between sections $S_M$ and $S_D$, such as to prevent kinking of shaft 401 at the transition. Manifold 700*d* is described in further detail herein in reference to FIGS. 3A and 3B.

Shaft 401 of FIGS. 2A and 2B has been described in terms of a shaft with at least a portion with a continuously varying stiffness (e.g. lower stiffness at distal locations), or a shaft with three or four sections with different stiffnesses (e.g. successively lower stiffnesses in each more distal section). In some embodiments, shaft 401 comprises two sections with different stiffnesses, such as a proximal section with a greater stiffness than a distal section, such as to improve trackability as described herein. In some embodiments, shaft 401 comprises four, five, six or more sections with different stiffnesses (e.g. successively lower stiffnesses in each more distal section), such as to improve trackability as described herein.

Figure 5B:
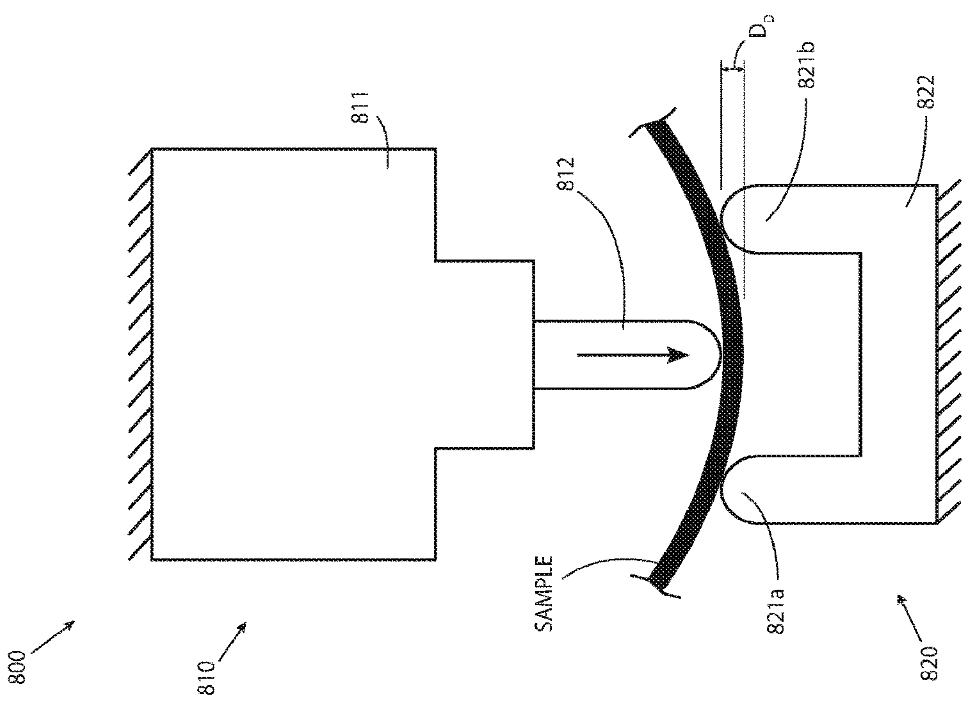
FIGS. 5A and 5B illustrate side views of an elongate sample being tested in a test fixture, consistent with the present inventive concepts.
Figure 5B:

In some embodiments, sections $S_P$, $S_M$, and/or $S_D$ each comprise a stiffness as defined by a stiffness test performed by a test fixture, such as test fixture 800 described herein in reference to FIG. 5. The "required bending force" described herein is defined by the force required to cause the midpoint of a two-inch span of the section of shaft assembly 400 to deflect approximately 0.125" (as described herein in reference to FIG. 5). In some embodiments, section $S_P$ of shaft assembly 400 comprises a stiffness with a required bending force of at least 10 lbf, such as at least 13 lbf, such as 16 lbf. Section $S_M$ of shaft assembly 400 can comprise a stiffness with a required bending force of at least 8 lbf, such as at least 10 lbf, such as 11 lbf. Section $S_D$ of shaft assembly 400 can comprise a stiffness with a required bending force of no more than 14 lbf, such as no more than 11 lbf, such as no more than 8 lbf, such as no more than 5 lbf. In some embodiments, section $S_M$ comprises a required bending force of at least 3 lbf more than the required bending force of section $S_D$. In some embodiments, section $S_P$ comprises a required bending force of at least 4 lbf more than the required bending force of section $S_M$. In some embodiments, section $S_P$ comprises a required bending force of at least 7 lbf more than the required bending force of section $S_D$.

Figures 3A, 3B:
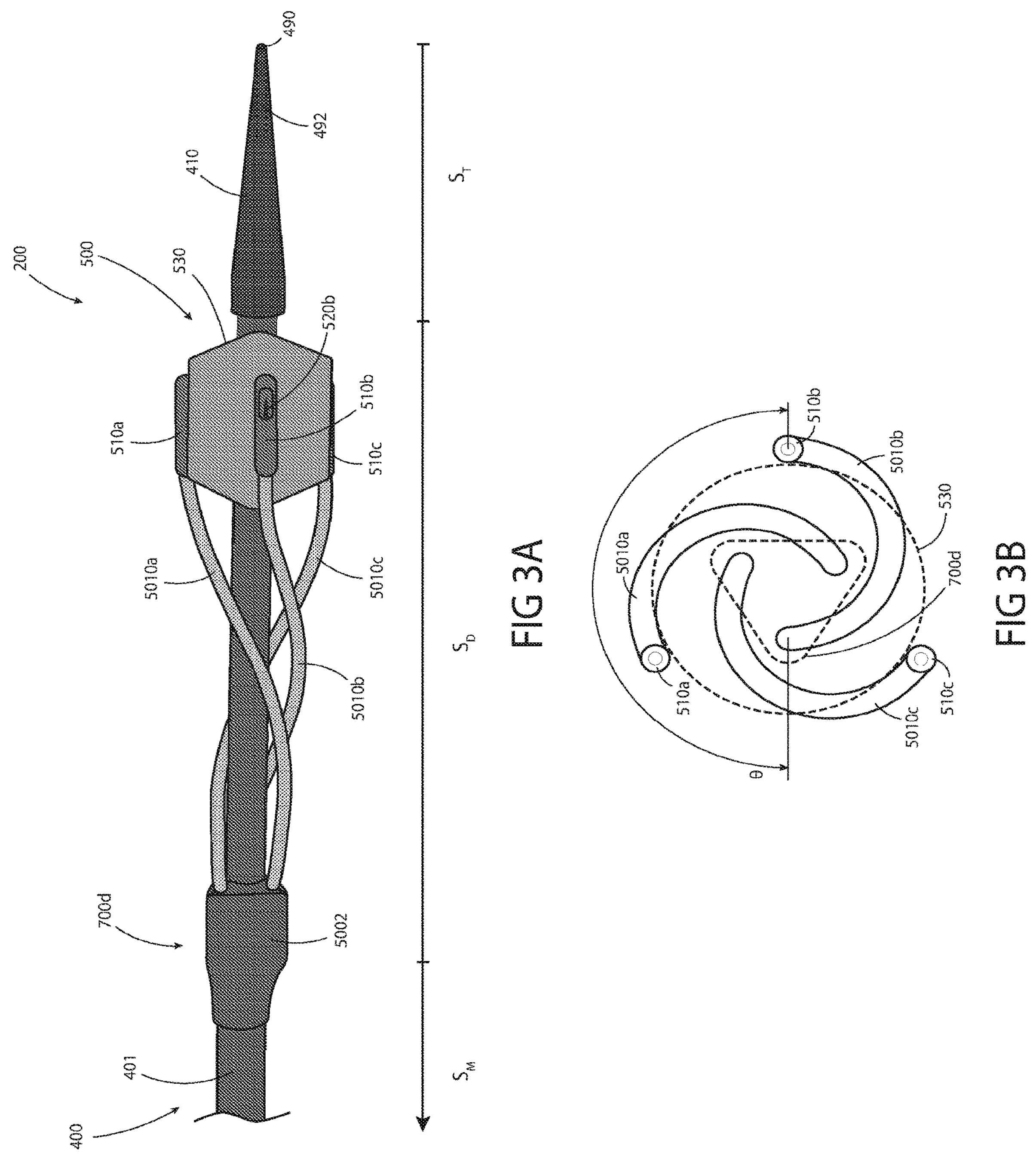
FIGS. 3A and 3B illustrate a side view and an end view of the distal portion of a catheter for treating tissue, consistent with the present inventive concepts.

Referring now to FIGS. 3A and 3B, a side view and an end view of the distal portion of a catheter for treating tissue are illustrated, respectively, consistent with the present inventive concepts. Catheter 200 includes shaft assembly 400 and functional assembly 500, and other components of similar construction and arrangement to those described herein. Shaft assembly 400 comprises a multi-lumen shaft, shaft 401, and a distal tip, tip 410. Shaft assembly 400 can comprise one or more ports, port 490 shown, a port configured to allow a guidewire, such as guidewire 60, to exit shaft 401. Port 490 is operably attached to a lumen of shaft 401, lumen 492 shown, through which a guidewire can be inserted. In some embodiments, lumen 492 extends between port 490 and a more proximal opening, such as an opening proximate the distal end of functional assembly 500, the proximal end of functional assembly 500, and/or manifold 700*d* (described herein), such that catheter 200 can be inserted into the patient over guidewire 60 in a "rapid exchange" manner. Alternatively or additionally, a guidewire 60 lumen can extend to a proximal end of catheter 200, such as to a location proximate but distal to handle 300 and/or within handle 300, such as to support a standard "over-the-wire" delivery of catheter 200.

Catheter 200 further includes manifold 700*d*, including housing 5002, which provides fluid connections between various lumens and other conduits within shaft 401 (proximal to manifold 700*d*) to various lumens and other conduits that provide and/or remove fluid to and/or from functional assembly 500. Functional assembly 500 can comprise a radially expandable and contractible element, expandable element 530 (e.g. a balloon as described herein). Positioned on expandable element 530 are one, two, three, or more tissue capture chambers 510 (e.g. three chambers 510*a-c* shown). Chambers 510*a-c* are each fluidly attached to a separate multi-lumen shaft, conduits 5010*a-c* respectively. In some embodiments, conduits 5010*a-c* each comprise at least two lumens (e.g. a lumen for a tube fluidly connected to an injectate delivery conduit 5010 and a lumen for providing a vacuum to a tissue capture chamber 510). Conduits 5010*a-c* are each fluidly attached to manifold 700*d*. A translatable needle or other fluid delivery element, injectate delivery element 520*a-c*, can be positioned in each respective chamber 510*a-c*. In some embodiments, conduits 5010*a-c* each comprise a material with a durometer less than or equal to the durometer of section $S_D$ of shaft 401, as described herein. For example, conduits 5010*a-c* can each comprise a material with a durometer of approximately 40 D. Manifold 700*d*, conduits 5010, and functional assembly 500 can be of similar construction and arrangement to similar components described in applicant's co-pending U.S. patent application Ser. No. 16/742,645, entitled "Intestinal Catheter Device and System", filed Jan. 14, 2020.

In some embodiments, and as shown in FIGS. 3A and 3B, conduits 5010*a-c* comprise a spiral geometry positioned about shaft 401 (e.g. a clockwise and/or a counterclockwise spiral). Conduits 5010*a-c* each attach to a separate chamber 510*a-c*, respectively. Chambers 510*a-c* are positioned at an angle θ relative to where the proximal end of conduit 5010 exits manifold 700*d* (angle θ shown in FIG. 3B). In some embodiments, angle θ comprises an angle of approximately 180°. In some embodiments angle θ is at least 25°, such as at least 50°, or at least 100°. In some embodiments, conduits 5010*a-c* comprise a biased shape, such as a shape created via a heat set (e.g. as described herein). Conduits 5010*a-c* can comprise a biased shape configured to minimize stress (e.g. torsional stress) between manifold 700*d* and chambers 510*a-c* (e.g. stress caused by conduits 5010*a-c* on chambers 510*a-c* as catheter 200 flexes while advanced through the anatomy of the patient). In some embodiments, the biased shape of conduits 5010*a-c* comprises an "S" like shape. Additionally or alternatively, the biased shape can comprise a twist along the length of conduit 5010. In some embodiments, for example when angle θ comprises an angle of approximately 180°, conduit 5010 can comprise a bend (e.g. a heat set bend) without a twist (e.g. the orientation of chamber 510 matches the orientation of the one or more lumens of conduit 5010 without the need for a twist between manifold 700*d* and chamber 510 when angle θ is approximately 180°).

Figure 4:
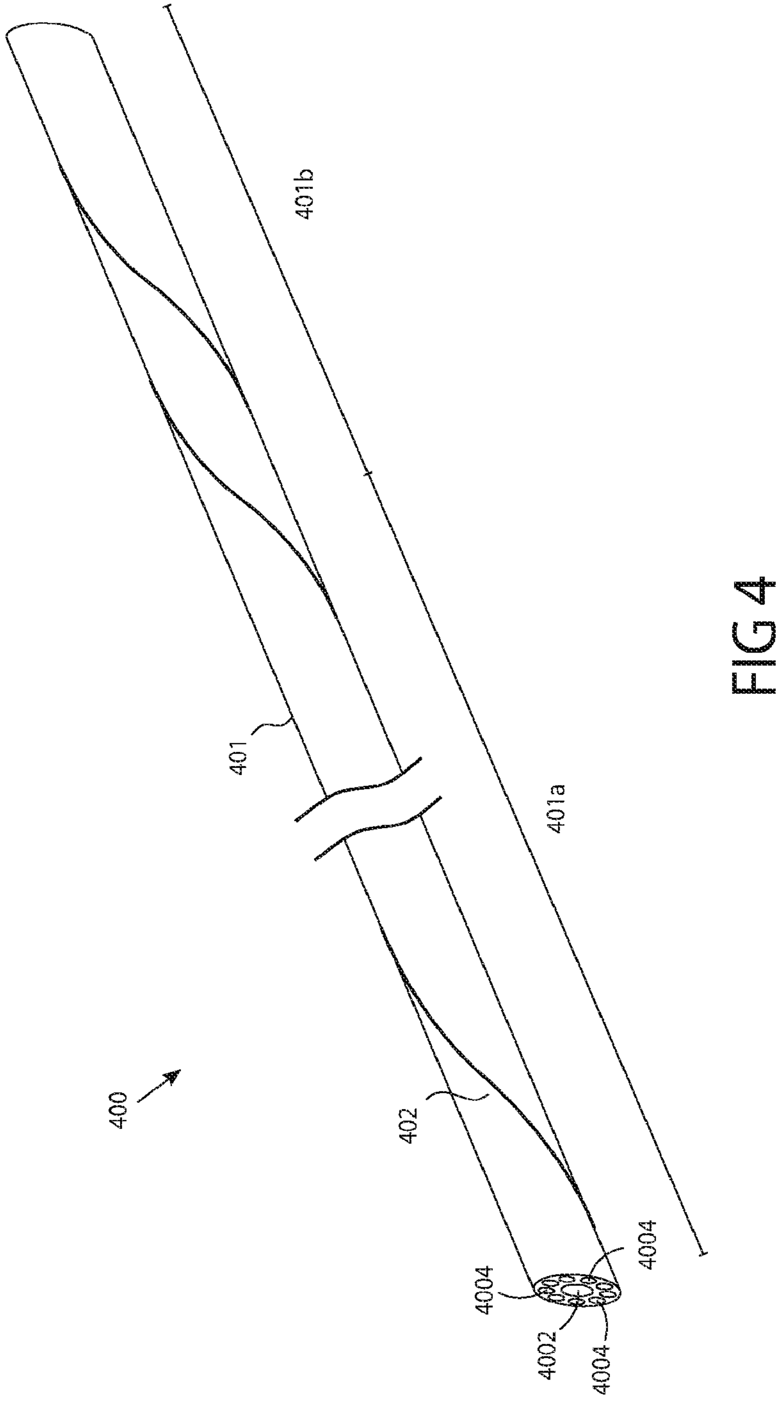
FIG. 4 illustrates a perspective view of a portion of a shaft assembly of a catheter for treating tissue, consistent with the present inventive concepts.

Referring now to FIG. 4, a perspective view of a portion of shaft assembly 400 is illustrated, consistent with the present inventive concepts. Shaft 401 of FIG. 4 comprises a single shaft including multiple satellite lumens (e.g. lumens 4004 shown) positioned about a central lumen 4002. Specifically, the multiple satellite lumens 4004 can be configured to slidingly receive one or more conduits, such as conduit 521 described herein. It can be desirable to equalize the path length of each lumen 4004 from the distal end of shaft 401 to the proximal end of shaft 401 (e.g. while shaft 401 transverses a tortuous path, such as a path through the duodenum or other portion of the gastrointestinal tract of a patient). Additionally or alternatively, it can be desirable to normalize the stiffness of shaft 401 along the length of shaft 401 at different bend planes (e.g. such that no bend shape is significantly favorable over any other along at least a portion of shaft 401). Shaft 401 can comprise a twisted geometry (e.g. a clockwise and/or a counterclockwise twist) along its length, such that each satellite lumen 4004 travels in a spiral pattern around the central axis of shaft 401. In some embodiments, shaft 401 comprises a counterclockwise twist, as shown in FIG. 4, such as to minimize path length differences encountered in the GI tract (e.g. a twist opposite to the inherent clockwise path encountered when positioned through the stomach and into the small intestine). In some embodiments, the outer surface of shaft 401 can comprise an indicator, marker 402, such as an elongate stripe along the shaft 401 that is aligned with a single satellite lumen. One or more markers 402 can provide a visual indicator of the twist in shaft 401. One or more markers 402 can provide a radial indicator of an internal lumen of shaft 401.

In some embodiments, shaft 401 comprises a twist with a varying pitch along its length. For example, shaft 401 can comprise a proximal portion 401*a* that comprises a first length and a first pitch, and a distal portion 401*b* that comprises a second length and a second pitch, where the second length is different than the first length and/or the second pitch is different than the first pitch. Note that proximal portion 401*a* and distal portion 401*b* are not necessarily shown to scale in FIG. 4. In some embodiments, the second pitch is lower than the first pitch (i.e. distal portion 401*b* comprises more twist per unit length than proximal portion 401*a*). In some embodiments, proximal portion 401*a* comprises a single twist (360°) and is approximately three times the length of distal portion 401*b* which comprises a single twist (360°). Either or both twists can comprise a counterclockwise twist (as shown in FIG. 4), which can be configured to minimize pathway length differences of tubular components within shaft 401 as described herein. In some embodiments, at least a portion of shaft 401 comprises a twist with a pitch of at least 0.5 twists per 72", such as at least 1 twist per 72", such as at least 3.5 twists per 72".

In some embodiments, the twist imparted on shaft 401 is created in a heat-setting process in which shaft 401 is maintained in a fixture in a twisted state while heat is applied. Additionally or alternatively, the twist imparted on shaft 401 can be created during an extrusion process (e.g. as shaft 401 is extruded, the extrusion is twisted at a prescribed rate) to produce a shaft with a "natural" twist. Alternatively, using a multi-tube construction (e.g. instead of a multi-lumen extrusion), satellite "tubes" can be twisted about a central tube (comprising central lumen 4002), and the twisted satellite tubes can be laminated (reflowed) to the central tube in the twisted configuration.

Shaft 401 can comprise a clockwise and/or counterclockwise twist. In some embodiments, shaft 401 comprises a counterclockwise twist (as shown in FIG. 4) configured to minimize pathway length difference of tubular components within shaft 401 as described herein. In some embodiments, shaft 401 can be similar to similar components described in applicant's co-pending U.S. patent application Ser. No. 16/742,645, entitled "Intestinal Catheter Device and System", filed Jan. 14, 2020.

Figure 5A:
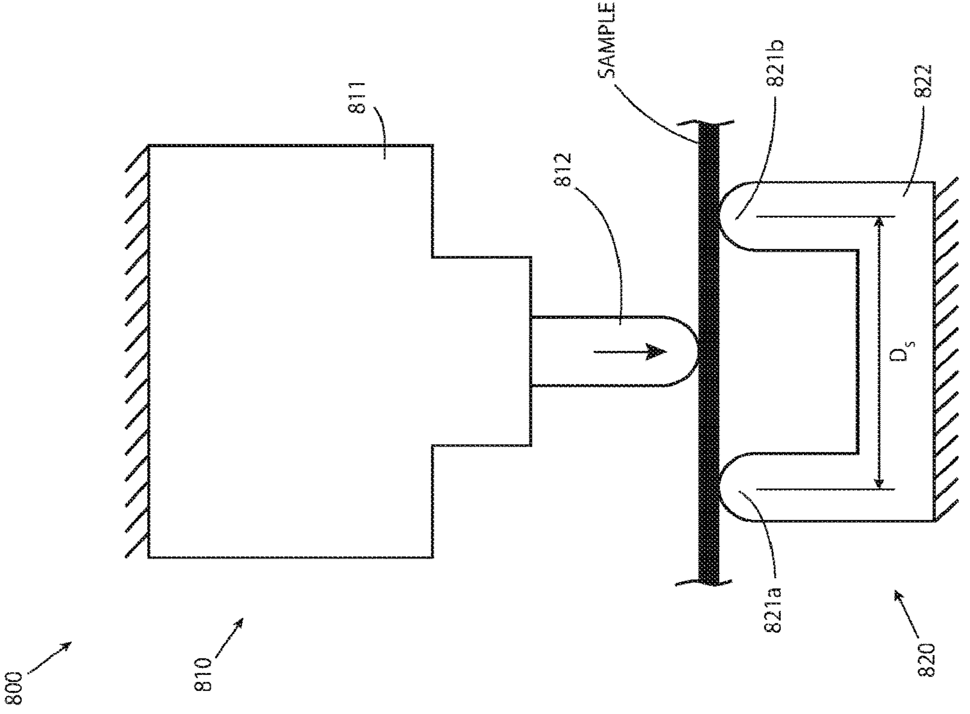

Referring now to FIGS. 5A and 5B, side views of an elongate sample being tested in a test fixture are illustrated. As described herein, the stiffness of a portion of an elongate object can be defined by the results of a test performed on that portion of the device utilizing a test fixture according to the present inventive concepts. Test fixture 800 comprises an actuator assembly 810 and a support assembly 820. Actuator assembly 810 comprises a housing 811, and a piston 812 configured to extend from housing 811. Support assembly 820 comprises two support arms 821*a* and 821*b*, each extending from a base 822. Support arms 821*a,b* are separated by a distance $D_S$, as shown. Actuator assembly 810 is positioned relative to support assembly 820 such that piston 812 is positioned equidistant between support arms 821*a* and 821*b*. In some embodiments, test fixture 800 includes an off-the-shelf tensile tester, such as a Chatillon tensile tester, and piston 812 and support assembly 820 comprise attachments configured to operably attach to the tensile tester. Alternatively or additionally, actuator assembly 810 can comprise one, two, or more sensors and/or processors configured to actuate piston 812 and/or to measure a force applied by piston 812 to a sample being tested (e.g. an elongate object, such as a section of shaft assembly 400 described herein).

Actuator assembly 810 can be configured to apply a force to an elongate object, object SAMPLE shown, via piston 812 while SAMPLE is supported by support arms 821*a* and 821*b*. Test fixture 800 can be configured to measure the force required to bend SAMPLE one or more bend distances, such as bend distance $D_D$ shown. Alternatively or additionally, test fixture 800 can be configured to apply a predetermined force(s) to SAMPLE and to measure the corresponding bend distance(s) to determine the stiffness of SAMPLE.

As described in reference to FIG. 2 herein, applicant has conducted testing using test fixture 800 to assess the stiffness of various sections of shaft assembly 400 of the present inventive concepts. In these tests, test fixture 800 was configured as follows: support arms 821*a,b* were separated by a distance $D_S$ of 1 inch; and each tested section of shaft assembly 400 was bent a distance $D_D$ of 0.125 inches. Results of the testing are described herein in reference to FIG. 2.

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A device for performing a medical procedure in the intestine of a patient comprising:

a guidewire;

an elongate shaft assembly comprising:

a shaft assembly first section comprising a distal section of the shaft assembly;

a shaft assembly second section proximal to the shaft assembly first section;

a shaft assembly third section proximal to the shaft assembly second section; and a shaft assembly fourth section comprising a distal tip;

a functional assembly positioned on the shaft assembly first section, the functional assembly comprising an expandable element configured to expand to a diameter of at least 18 mm; and a guidewire lumen configured to slidingly receive the guidewire, wherein the shaft assembly first section terminates at a distal end of the functional assembly, wherein the distal tip comprises a tapered portion of the shaft assembly extending beyond the distal end of the functional assembly, wherein the distal tip comprises a proximal tip segment and a distal tip segment, wherein the distal tip segment comprises a smaller diameter than the proximal tip segment, wherein a taper and/or a wall thickness variation of the distal tip configures the proximal tip segment to have a stiffness greater than a stiffness of the guidewire and the distal tip segment to have a stiffness less than the stiffness of the guidewire, and wherein a proximal end of the distal tip has a stiffness approximately equal to a stiffness of a distal end of the shaft assembly first section.

2. The device according to claim 1, wherein the shaft assembly comprises a multi lumen shaft.

3. The device according to claim 2, wherein the shaft assembly further comprises at least one conduit positioned within a lumen of the multi lumen shaft.

4. The device according to claim 1, wherein the shaft assembly first section comprises a length of at least 2 inches.

5. The device according to claim 1, wherein the shaft assembly second section comprises a length of at least 10 inches.

6. The device according to claim 1, wherein the shaft assembly third section comprises a length of at least 32 inches.

7. The device according to claim 1, wherein the shaft assembly third section is longer than the shaft assembly second section and the shaft assembly second section is longer than the shaft assembly first section.

8. The device according to claim 1, wherein the shaft assembly first section comprises a material with a durometer of approximately 40D, the shaft assembly second section comprises a material with a durometer of approximately 55D, and the shaft assembly third section comprises a material with a durometer of approximately 63D.

9. The device according to claim 1, wherein the shaft assembly third section comprises a length of approximately 57 inches, the shaft assembly second section comprises a length of approximately 10 inches, and the shaft assembly first section comprises a length of approximately 5 inches.

10. The device according to claim 9, wherein the shaft assembly first section comprises a material with a durometer of approximately 40D, the shaft assembly second section comprises a material with a durometer of approximately 55D, and the shaft assembly third section comprises a material with a durometer of approximately 63D.

11. The device according to claim 1, wherein the functional assembly is configured to expand tissue within the intestine of the patient.

12. The device according to claim 1, wherein the functional assembly is configured to ablate tissue within the intestine of the patient.

13. The device according to claim 1, wherein the functional assembly is configured to expand and ablate tissue within the intestine of the patient.

14. The device according to claim 1, wherein the functional assembly comprises a balloon configured to ablate tissue within the intestine of the patient with a hot fluid.

15. The device according to claim 1, further comprising an injection assembly including at least one needle, at least one port, and at least one fluid delivery tube.

16. The device according to claim 1, further comprising a fluid manifold secured across a transition between the shaft assembly second section and the shaft assembly first section, the fluid manifold being configured to route inflow and return flow to the functional assembly and to mechanically reinforce the transition against kinking.

17. The device according to claim 1, wherein a distal-most portion of the distal tip comprises a material having a durometer of less than 40D.

* * * * *